US012740961B2

(12) United States Patent
Grandemange et al.

(10) Patent No.: US 12,740,961 B2
(45) Date of Patent: Sep. 22, 2026

(54) USE OF AN ORGANOMETALLIC COMPOUND AS A DNA-DEMETHYLATING AGENT

(71) Applicants: UNIVERSITE DE LORRAINE, Nancy (FR); INSTITUT NATIONAL DE LA SANTÉ ET DE LA RECHERCHE MÉDICALE—INSERM, Paris (FR)

(72) Inventors: Stéphanie Grandemange, Laneuveville devant Nancy (FR); Antonio Monari, Nancy (FR); Philippe Gros, Tonnoy (FR); Pierre François Cartron, Reze (FR)

(73) Assignees: UNIVERSITE DE LORRAINE, Nancy (FR); INSTITUT NATIONAL DE LA SANTÉ ET DE LA RECHERCHE MÉDICALE—INSERM, Paris (FR)

( * ) Notice: Subject to any disclaimer, the term of this patent is extended or adjusted under 35 U.S.C. 154(b) by 1025 days.

(21) Appl. No.: 17/292,689

(22) PCT Filed: Nov. 12, 2019

(86) PCT No.: PCT/FR2019/052689
§ 371 (c)(1),
(2) Date: May 10, 2021

(87) PCT Pub. No.: WO2020/099777
PCT Pub. Date: May 22, 2020

(65) Prior Publication Data

US 2022/0031652 A1 Feb. 3, 2022

(30) Foreign Application Priority Data

Nov. 12, 2018 (FR) ....................................... 1860412

(51) Int. Cl.

| | |
|---|---|
| ***A61P 9/00*** | (2006.01) |
| ***A61K 8/19*** | (2006.01) |
| ***A61K 8/49*** | (2006.01) |
| ***A61K 31/295*** | (2006.01) |
| ***A61P 25/00*** | (2006.01) |
| ***A61P 29/00*** | (2006.01) |
| ***A61P 35/00*** | (2006.01) |
| ***A61P 35/02*** | (2006.01) |
| ***A61Q 19/00*** | (2006.01) |
| ***A61Q 19/06*** | (2006.01) |

(52) U.S. Cl.
CPC ............ *A61K 31/295* (2013.01); *A61P 35/02* (2018.01)

(58) Field of Classification Search
CPC .. A61P 9/00; A61P 25/00; A61P 29/00; A61P 35/00; A61P 35/02; A61K 8/19; A61K 8/49; A61K 8/4926; A61K 31/295; A61K 2800/58; A61Q 19/00; A61Q 19/06
See application file for complete search history.

(56) References Cited

FOREIGN PATENT DOCUMENTS

| | | |
|---|---|---|
| FR | 1 463 870 | 7/1966 |
| WO | 00/29036 | 5/2000 |
| WO | 2006/120133 | 11/2006 |
| WO | 2014/040826 | 3/2014 |

OTHER PUBLICATIONS

Zohreh Naseri et al., First row transition metal complexes of thienyl substituted terpyridine; structural, photo physical and biological studies Polyhedron, vol. 33, No. 1, Dec. 13, 2011, pp. 396-403. (Year: 2011).*

Uttara Basu et al: "Nuclear targeting terpyridine iron (I) complexes for cellular imaging and remarkable photocytotoxicity" Journal of Inorganic Biochemistry, vol. 116, Nov. 1, 2012, pp. 77-87 (Year: 2012).*

Bonacin et al., Electrocatalytic Activity in Sensing of Nitrite by Films Produced by Electropolymerization of [Fe(Br-ph-tpy)2]2+, Journal of Coordination Chemistry, vol. 70, No. 7, pp. 1137-1145 (Year: 2017).*

Constable et al., "Multinucleating 2,2' : 6',2"-Terpyridine Ligands as Building Blocks for the Assembly of Co-ordination Polymers and Oligomers," J. Chem. Soc. Dalton Trans. 1992, pp. 3467-3475.

Krass et al., "Immobilization of IT-Assembled Metallo-Supramolecular Arrays in Thin Films: From Crystal-Engineered Structures to Processable Materials," Angew. Chem. Int. Ed. vol. 40, 2001, pp. 3862-3865.

Leonhardt et al., "A Targeting Sequence Directs DNA Methyltransferase to Sites of DNA Replication in Mammalian Nuclei," Cell, vol. 71, Nov. 27, 1992, pp. 865-873.

Basu et al., "Nuclear targeting terpyridine iron(II) complexes for cellular imaging and remarkable photocytotoxicity," Journal of Inorganic Biochemistry 116, 2012, pp. 77-87, updated Jul. 2019, 2 pages.

Zhou et al., "Zebularine: A Novel DNA Methylation Inhibitor that Forms a Covalent Complex with DNA Methyltransferases," J Mol Biol., Aug. 23, 2002, pp. 591-599.

Amato, "Inhibition of DNA Methylation by Antisense Oligonucleotide MG98 as Cancer Therapy," Clinical Genitourinary Cancer, Dec. 2007, pp. 422-426.

Bird, "DNA methylation patterns and epigenetic memory," Genes & Development, 2002, Cold Spring Harbor Laboratory Press, pp. 6-21.

(Continued)

*Primary Examiner* — Brenda L Coleman
(74) *Attorney, Agent, or Firm* — NIXON & VANDERHYE

(57) ABSTRACT

Disclosed is the non-therapeutic use, as a DNA-demethylating agent, of at least one organometallic compound including an iron atom bound to two terpyridine groups. Further disclosed are method related to applying such agent as medicine.

11 Claims, 13 Drawing Sheets

(56) References Cited

OTHER PUBLICATIONS

Figure 1:
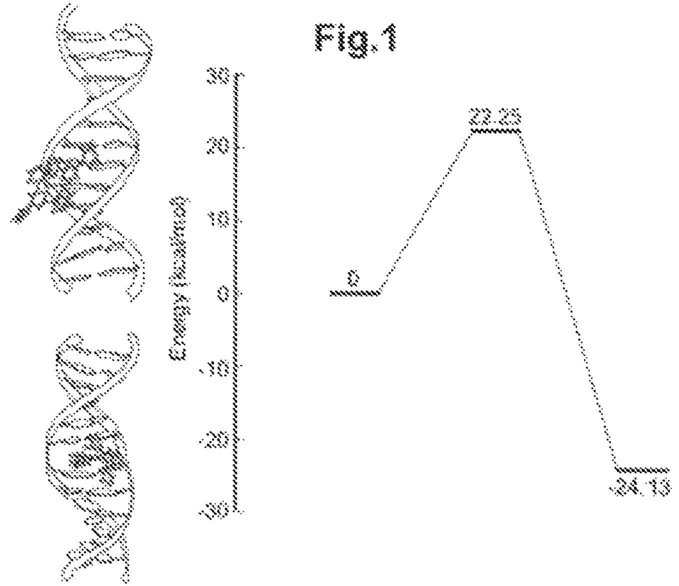

Bonate et al., "Discovery and development of clofarabine: a nucleoside analogue for treating cancer," Nature Reviews, Drug Discovery, vol. 5, Oct. 2006, pp. 855-863.
Cheng et al., "Inhibition of DNA Methylation and Reactivation of Silenced Genes by Zebularine," Journal of the National Cancer Institute, vol. 95, No. 5, Mar. 5, 2003, pp. 399-409.
Cheng et al., "Preferential response of cancer cells to zebularine," Cancer Cell, vol. 6, Aug. 2004, pp. 151-158.
Cheray et al., "Specific inhibition of one DNMT1-including complex influences tumor initiation and progression," Short Report, Open Access, Clinical Epigenetics, BioMed Central, 2013, 7 pages.
Cheray et al., "Specific inhibition of DNMT1/CFP1 reduces cancer phenotypes and enhances chemotherapy effectiveness," Research Article, Epigenomics, 2014, vol. 6, No. 3, pp. 267-275.
Cuthbert et al., "Histone Deimination Antagonizes Arginine Methylation," Cell, vol. 118, Sep. 3, 2004, pp. 545-553.
Herman et al., "Inactivation of the CDKN2/p16/MTSJ Gene is Frequently Associated with Aberrant DNA Methylation in all Common Human Cancers," Cancer Research, vol. 55, Oct. 15, 1995, pp. 4525-4530.
Hervouet et al., "Disruption of Dnmt1/PCNA/UHRF1 Interactions Promotes Tumorigenesis from Human and Mice Glial Cells," PLOS ONE, vol. 5, No. 6, Jun. 2010, 14 pages.
Jeha et al., "Clofarabine, a novel nucleoside analog, is active in pediatric patients with advanced leukemia," Blood, vol. 103, No. 3, Feb. 1, 2004, pp. 784-789.
Liu et al., "Growth Stunting in Early Life in Relation to the Onset of the Childhood Component of Growth," Journal of Pediatric Endocrinology & Metabolism, vol. 11, 1998, pp. 247-260.
Okano et al., "DNA Methyltransferases Dnmt3a and Dnmt3b are Essential for De Novo Methylation and Mammalian Development," Cell, vol. 99, Oct. 29, 1999, pp. 247-257.
Santini et al., "Changes in DNA Methylation in Neoplasia: Pathophysiology and Therapeutic Implications," Annals of Internal Medicine, vol. 134, No. 7, Apr. 3, 2001, pp. 573-586.
Winquist et al., "Phase II trial of DNA methyltransferase 1 inhibition with the antisense oligonucleotide MG98 in patients with metastatic renal carcinoma: A National Cancer Institute of Canada Clinical Trials Group investigational new drug study," Invest New Drugs, 2006, pp. 159-167.
International Search Report for PCT/FR2019/052689 dated Apr. 8, 2020, 7 pages.
Written Opinion of the ISA for PCT/FR2019/052689 dated Apr. 8, 2020, 5 pages.
Naseri et al., "First row transition metal complexes of thienyl substituted terpyridine: Structural, photophysical and biological studies", Polyhedron, Nov. 30, 2011, vol. 33, No. 1, pp. 396-403, 8 total pages.
Basu et al., "Nuclear targeting terpyridine iron(II) complexes for cellular imaging and remarkable Photocytotoxicity", Journal of Inorganic Biochemistry, Nov. 1, 2012, vol. 116, pp. 77-87, 11 total pages.

* cited by examiner

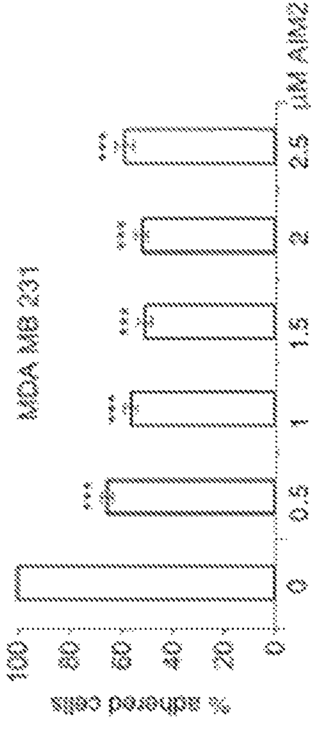
Fig.6
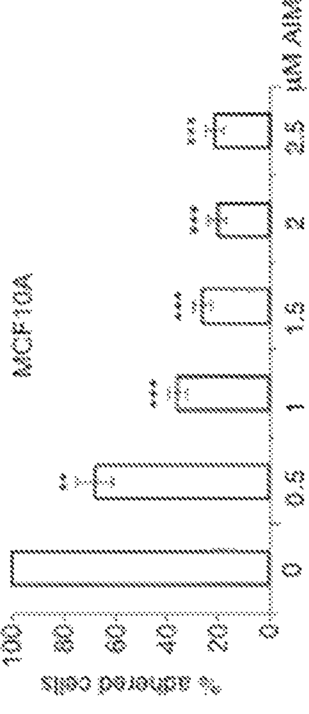
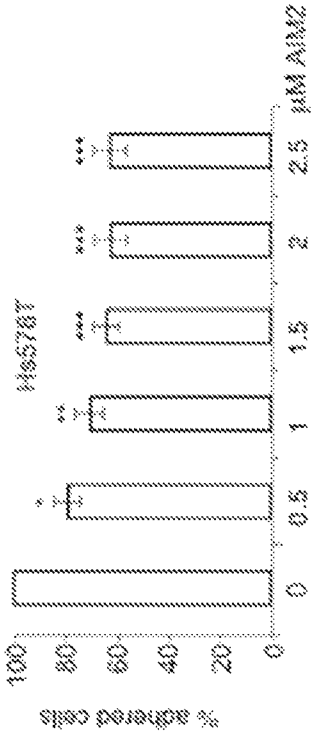

48h of treatment with 5Fu or with doxo

Untreated cells

Without ttt

Cells pre-treated with AIM for 72h

+ AIM 2μM 24h 48h 72h → Count

Ru
AIM1
AIM2
AIM3

USE OF AN ORGANOMETALLIC COMPOUND AS A DNA-DEMETHYLATING AGENT

CROSS-REFERENCE TO RELATED APPLICATIONS

This application is the U.S. national phase of International Application No. PCT/FR2019/052689 filed Nov. 12, 2019 which designated the U.S. and claims priority to FR 1860412 filed Nov. 12, 2018, the entire contents of each of which are hereby incorporated by reference.

TECHNICAL FIELD OF THE INVENTION

The present invention generally relates to the non-therapeutic use and the therapeutic use of compounds having a demethylating effect on DNA.

It thus firstly relates to the non-therapeutic use as a DNA-demethylating agent of iron-based organometallic complexes to form, for example, biotechnology tools, such as sequencing reagents.

Then, the invention is also based on the therapeutic use of these iron-based organometallic complexes as medicine, for example for the treatment of proliferative pathologies, in particular, cancers.

TECHNOLOGICAL BACKGROUND

Cancers are the second highest cause of death after cardiovascular diseases in industrialized countries. Except for direct DNA mutations of essential genes, the progression of a cancer cell is frequently associated with epigenetic modifications, i.e. not directly coded by the DNA sequence.

The term "epigenetic" indeed groups together a whole set of modifications responsible for the regulation of gene expression which could be transmitted during cell division and which involve no change in the DNA sequence (Flintoft, 2017). This terms thus groups together different processes, such as DNA methylation, post-translational modifications of histones and non-coding RNA expression.

The regulation of gene expression is a phenomenon which impacts more aspects of cell biology (embryogenesis, development, cell differentiation, as well as cell death) in multi-cell organisms. A deregulation of epigenetic modifications, both at the level of maintaining them and in the coordination thereof, is frequently observed for various pathologies, such as inflammation, obesity, neurodegenerative and cardiovascular diseases, as well as cancers. Consequently, searching for molecules capable of regulating these processes is of significant interest.

In particular, DNA methylation is an epigenetic process. It is the result of a methylation of cytosines in 5-methylcytosines in C-G dimers of DNA, in particular in CpG islands. Around 80% of these regions are methylated in the human genome. DNA methyltransferases (DNMTs) enzymes catalyse the addition of a methyl group coming from the S-Adenosylmethionine donor on the carbon 5 of a cytosine. Among DNA methyltransferases, DNMT1 which is an enzyme involved in maintaining the epigenetic information (Leonhardt et al., 1992; Liu et al., 1998), takes as a model, the DNA strand semi-methylated during the replication, while the DNMT3a and 3b enzymes can act on a non-methylated strand and therefore modify the epigenetic information (Okano et al., 1999). However, DNMT2 does not show any DNA methyltransferase activity. DNA methylation leads to the repression of gene expression (Bird, 2002).

There is also an enzyme (peptidyl arginine deiminase 4) which could, by deiminating the arginine residues of histone H3, interfere with methylation (Cuthbert et al., 2004).

To date, the development of DNA-demethylating agents (also known by the term, "DNA hypomethylating agent") is based on strategies leading to an indirect demethylation of DNA and this, in particular via the inhibition of enzymes responsible for the methylation of it, namely the DNMTs described above.

For example, for numerous cancers, it has demonstrated that certain tumour-suppressing genes, like for example p16, were hypermethylated (Herman et al., 1995). The consequence of this hypermethylation is the inactivation of this cell cycle regulating gene. It has demonstrated that the inhibitors blocking the DNA methyltransferase activity cause the hypomethylation of these tumour-suppressing genes and thus have anticancer properties (Santini et al., 2001).

Currently, the different DNA-demethylating agents can be classified according to the action mode thereof in five different categories: 1) non-methylatable nucleoside analogues (decitabine, azacytidine), 2) catalytic activity inhibitors (procainamide), 3) S-adenosylmethionine hydrolase inhibitors (cladribine), 4) DNMTs expression inhibitors (MG98) and 5) inhibitors of interaction of DNMTs with the partners thereof (UP peptide).

1) Non-methylatable nucleoside analogues, such as 5-azacytidine, Decitabine (DAC or 5-aza-2'-deoxycytidine), Zebularine (dZTP), 5-fluoro-2'-deoxycytidine (FdCyd), SGI-110 (modified Decitabine) and CP-4200 (a derivative of 5-azacytidine) make it possible to capture DNMTs on the DNA having incorporated these analogues thus leading to the degradation thereof. However, these non-methylatable nucleoside analogues, like 5-azacytidine, or 5-aza-2'-deoxycytidine, in addition to having significant side effects, generally show a high toxicity and a low stability. Zebularine however has a better stability (Zhou et al., 2002; Cheng et al., 2003) and a lower toxicity (Cheng et al., 2004).

2) DNMTs enzymatic activity inhibitors (such as RG108, procaine, nanaomycin and procainamide) are synthetic compounds which have an affinity for CpG-rich DNA regions thus blocking DNMT1 activity. These molecules have several advantages with respect to nucleotide analogues, as the use thereof is not limited to highly proliferative cells, since they inhibit directly the DNMTs without requiring the incorporation thereof within the DNA.

3) S-adenosylhomocysteine hydrolase inhibitors themselves lead to a drop in S-adenosylmethionine which is the methyl donor making it possible for methyltransferases to catalyse the methylation of DNA cytosines (Cladribine, Fludarabine and Clofarabine) (Bonate et al., 2006; Jeha et al., 2004).

4) DNMTs synthesis inhibitors, such as antisense oligonucleotides and microRNAs (MG98) (Amato, 2007; Winquist et al., 2006) are based on the fact that a hypermethylation is very often associated with an increase of DNMTs expression. Despite a significant interest for this strategy, currently, phase I or II clinical trials have revealed a lack of effectiveness of these oligonucleotides.

5) Inhibitors of interaction of DNMTs with the partners thereof relate to peptide molecules which are capable of disrupting DNMTs with some of the protein partners thereof necessary for the functioning thereof. As protein complexes formed with DNMTs can vary according to target genes, this approach makes it therefore possible to avoid (with respect to the other action modes mentioned above) the induction of an overall hypomethylation which can be at the origin of significant side effects. It has, for example, been demonstrated that the specific inhibition of the DNMT3A/ISGF3γ complex makes it possible to re-establish a sensitivity to temozolomide and thus reduce the tumour growth of glioblastomas (Cheray et al., 2013, 2014; Hervouet et al., 2010).

To date, the search for molecules capable of modulating the level of DNA methylation is therefore focused only towards enzyme inhibitors responsible for this process, namely DNMTs.

It is also known from the state of the art, the publication by Zohreh Naseri et al. 2011, Pergamon Press, which discloses organometallic complexes comprising the ligand 4'-(2-thienyl)-2,2',6',2"-terpyridine. A solvate of a corresponding iron complex ($Fe(thioterpy)_2(NO_3)_2.MeOH$) is described as compound 3 in the publication. However, according to the results presented in this publication, this iron complex 3 has a marginal activity towards the microorganisms tested, does not demonstrate any cytotoxic effect on tested leukaemia and fibrosarcoma cell lines (table 7), and the superoxide ion trapping activity thereof is not noteworthy.

The publication by Uttara et al. 2012, Journal of Inorganic Biochemistry, describes photocytotoxic terpyridine irons (complexes 1, 1a, 2, 2a, 3 and 3a). According to the biological results provided, the complex 1 has the affinity of bonding to the weakest DNA from among the three complexes tested, has no DNA cleaving activity under UV-A or under green light.

Document FR 1 463 870 describes the use of organometallic complexes for colouring keratin materials.

In this context, there is a need in the state of the art to develop new DNA-demethylating agents for therapeutic and non-therapeutic purposes.

There is, in particular, a need in the state of the art to develop new DNA-demethylating agents which are effective, which preferably have reduced or less undesirable effects with respect to the demethylating agents of the prior art (preferably, low cell cytotoxicity), while being easy to implement and by advantageously having a moderate cost price.

An aim of the present invention is thus to propose new compounds which avoid, totally or partially, the above-mentioned disadvantages.

OBJECT OF THE INVENTION

The Applicant is thus connected to the development of new demethylating compounds capable of interacting with DNA.

They have in particular developed a new class of demethylating agents capable of leading to a direct demethylation of DNA by simple chemical reactions and this, in acellular and cellular systems.

The Applicant has indeed demonstrated that certain organometallic compounds comprising an iron atom bound to two terpyridine groups made a direct demethylation of DNA possible.

These compounds could in particular be used, whether for non-therapeutic applications, for example, as reaction reagents when a DNA demethylation is required, or for therapeutic applications.

In this case, the Applicant has demonstrated that the compounds according to the invention had an antiproliferative action, in particular on cancer cells. Furthermore, as the experimental tests show below (in particular, examples 9 and 10), the compounds according to the invention are non-cytotoxic and thus have a cytostatic effect.

To this end, the present invention aims for the non-therapeutic use, as DNA demethylating agent, of at least one organometallic compound comprising an iron atom bound to two terpyridine groups of the following general formula (I):

(I)

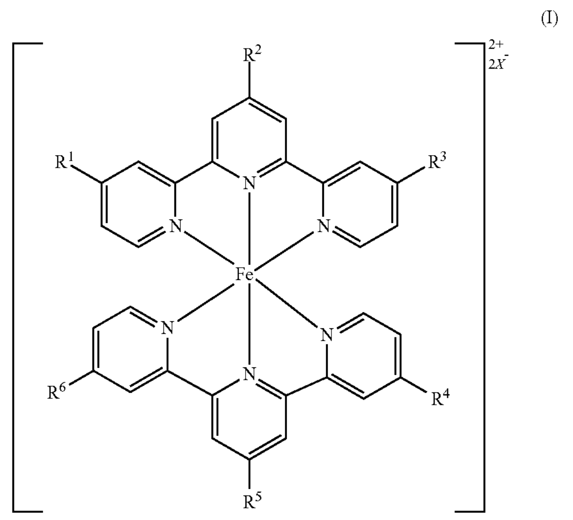

wherein:

$R^1$ to $R^6$, identical or different are chosen from among: a hydrogen atom; a linear or branched alkyl chain of formula $C_nH_{2n+1}$ with n=1 to 12; a COOH group; an $SO_3H$ group; a $PO_3H$ group; an aromatic cycle of formula (II) to (VI) below:

(II)

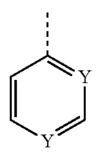

(III)

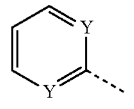

(IV)

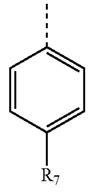

(V)

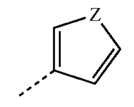

(VI)

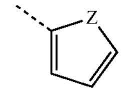

where

Y are each independently from the others, a CH group or a nitrogen atom (the two Y groups can be identical or different);

$R^7$ is chosen from among an $OC_yH_{2Y+1}$ group with y=1 to 10; $SC_wH_{2w+1}$ with w=1 to 10; $N(C_mH_{2m+1})_2$ with m=1 to 6, COOH; $SO_3H$ or $PO_2H_3$;

Z designates an oxygen atom, a sulphur atom or an NH group;

the dotted line represents a C—C bond at the level of the connection point of the aromatic cycle of formula (II) to (VI) to the terpyridine groups of the organometallic compound of formula (I);

$X^-$ is a counterion.

The present invention also aims for an organometallic compound comprising an iron atom bound to two terpyridine groups, having a general formula (I) defined above for use as medicine.

Finally, the present invention could be a pharmaceutical composition which could comprise, in a pharmaceutically acceptable carrier, at least one organometallic compound such as defined above.

For the remainder of the description, unless specified otherwise, the indication of an interval of values "from X to Y" or between "X and Y", in the present invention, is understood as including the values X and Y.

DETAILED DESCRIPTION OF AN EXAMPLE OF AN EMBODIMENT

The following description, given as non-limiting examples, will make it well understood what the invention consists of and how it can be achieved.

I. Non-Therapeutic Use of the Compound(s) of General Formula (I)

As mentioned above, the present invention is based on the non-therapeutic use of as DNA-demethylating agent, of at least one organometallic compound comprising an iron atom bound to two terpyridine groups of following general formula (I):

(I)

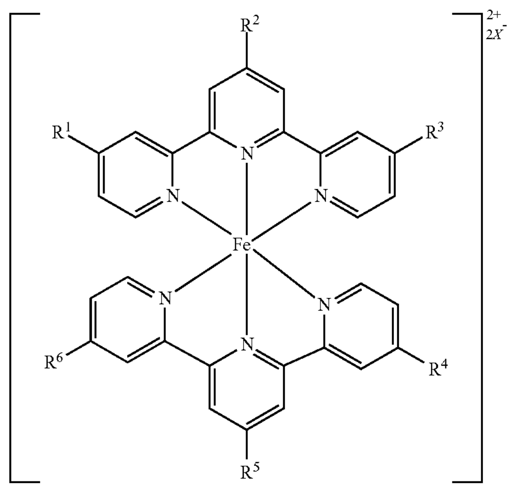

wherein:

$R^1$ to $R^6$, identical or different are independently chosen from among: a hydrogen atom, a linear or branched alklyl chain of formula $C_nH_{2n+1}$ with n=1 to 12; a COOH group, an $SO_3H$ group; a $PO_3H$ group; an aromatic cycle of formula (II) to (VI) below:

(II)

(III)

(IV)

(V)

(VI)

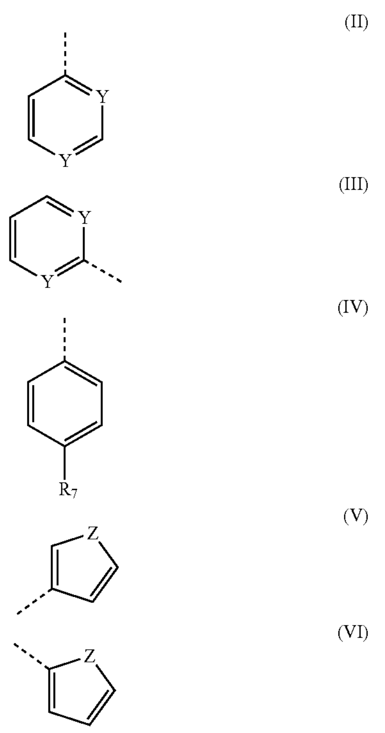

where

Y are each independently from the others, a CH group or a nitrogen atom, namely the two Y groups can be identical or different;

$R^7$ is chosen from among an $OC_yH_{2Y+1}$ group with y=1 to 10; $SC_wH_{2w+1}$ with w=1 to 10; $N(C_mH_{2m+1})_2$ with m=1 to 6, COOH; $SO_3H$; $PO_2H_3$;

Z designates an oxygen atom, a sulphur atom or an NH group;

the dotted line represents a C—C bond at the level of the connection point of the aromatic cycle of formula (II) to (VI) to the terpyridine groups of the organometallic compound of formula (I);

$X^-$ is a counterion.

According to the invention, the terpyridine groups are ligands particularly suitable for the iron atom which make it possible to form a relatively stable organometallic compound and which would be, resistant even in a biological environment. Furthermore, the particular configuration of terpyridine ligands gives a noteworthy rigidity to the organometallic compound according to the invention.

The compounds of the invention can be in the form of salts, solvates and/or pharmaceutically acceptable pro-drugs. Pro-drugs are variants of the compounds of the invention which can be transformed in vivo into compounds of general formula (I) according to the invention.

According to the invention, the term "pharmaceutically acceptable salts or solvates" refers to salts or solvates which conserve the desired biological activity such as described above of the organometallic compounds of the invention and which expose very little, even no undesired toxicological effect.

According to the invention, the term "alkyl" refers to a linear or branched, saturated or unsaturated hydrocarbon radical, having advantageously 1 to 12 carbon atoms, such as methyl, ethyl, propyl, isopropyl, butyl, isobutyl, tertbutyl, pentyl, neopentyl, n-hexyl, etc. Groups having 1 to 6 atoms and, in particular, 1 to 4 carbon atoms are preferred.

According to a first preferred embodiment, $R^1$ to $R^6$ can correspond to a hydrogen atom.

According to this embodiment, the organometallic compound of formula (I) can respond to the following formula (IX):

(IX)

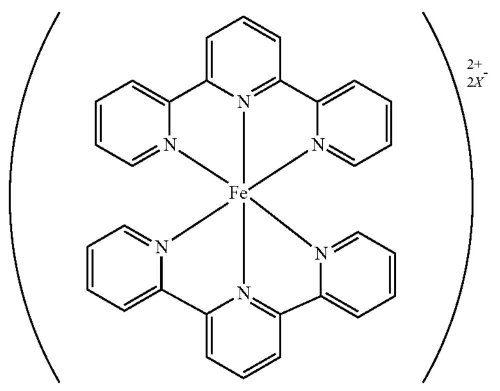

This compound of formula (IX) will be called below AIM1.

According to a second preferred embodiment, $R^1$, $R^3$, $R^4$, $6^6$ can be identical and correspond to a hydrogen atom, and $R^2$ and $R^5$ can be identical and designate an aromatic cycle of formula (II) such as described above with Y═CH and thus correspond to a benzene of following formula (VII):

(VII)

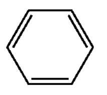

According to this embodiment, the organometallic compound of formula (I) can respond to the following formula (X):

(X)

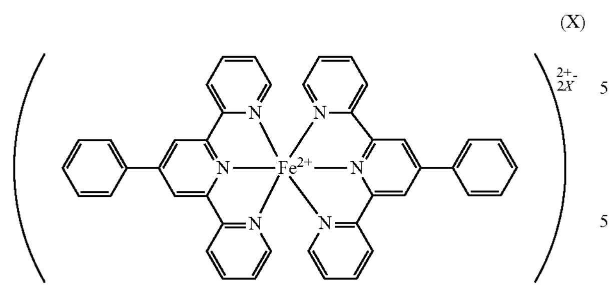

This compound of formula (X) will be called below AIM2.

According to a third preferred embodiment, $R^1$, $R^3$, $R^4$, $R^6$ are identical and correspond to a hydrogen atom, and $R^2$ and $R^5$ are identical and designate an aromatic cycle of formula (II) where one of the Y═CH and the other Y═N and correspond to a pyridine radical of following formula (VIII):

(VIII)

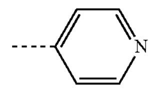

where the dotted line represents a C—C bond between the carbon carried by the pyridine radical and the carbon carried by the terpyridine group of the organometallic compound of formula (I).

According to this embodiment, the organometallic compound of formula (I) can respond to the following formula (XI):

(XI)

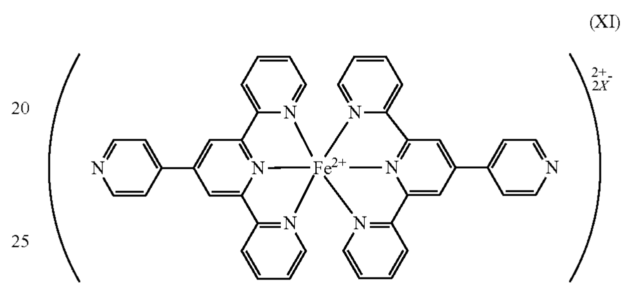

This compound of formula (XI) will be called below AIM3.

The two terpyridine groups of this compound AIM3 thus each carry a pyridinic core, the nitrogen atom making it possible to induce a nucleophilic effect.

According to an embodiment of the invention, the organometallic compound of formula (I) excludes the compound(s) where $R^1$═$R^3$═$R^4$═$R^6$═H and where $R^2$═$R^5$ is chosen from among an aromatic cycle of formula (VI), wherein Z is a sulphur atom or an aromatic cycle of formula (II) or (III) with Y═CH.

Preferably, the counterion $X^-$ is chosen from among: $Cl^-$, $Br^-$, $I^-$, hexafluorophosphate of formula $PF_6^-$, preferably the counterion is $PF_6^-$.

Advantageously, the organometallic compound(s) are capable of leading to a direct DNA demethylation.

Without being bound by any theory, it would seem that the DNA demethylation would be due, either to a nucleophilic attack of 5-methylcytosines (5mC) thus leading to the deamination thereof, and/or either to an oxidation mediated by iron which would make a conversion of 5mC into 5-hydroxymethylcytosine (5hmC) possible.

Thus, the organometallic compounds of formula (I) according to the invention can in particular be used in order to form biotechnology tools, for example as sequencing reagents where a DNA demethylation is required.

As an example, the compound(s) of the invention can be used as a biotechnology tool, like for example as a reagent to carry out in vitro demethylation experiments on cells, generally tumour cells, coming from a sample taken from an animal. These experiments would make it possible, for example, to confirm the presence or not of a DNA methylation phenomenon on certain genes, to block the cell proliferation and therefore sensitise them to chemotherapy agents. According to the invention, “animal” is understood as mammals, birds, fish, insects, etc., as well as human beings.

The synthesis of the organometallic compound(s) of formula (I) according to the invention and in particular the compounds AIM1 to AIM3 has been described above in publications, such as the publication by E. C. Constable, A. M. W. Cargill Thompson, Dalton Trans, 1992, 2947-2950 for the compounds AIM1 and AIM3 and the publication by H. Krass, E. A. Plummer, J. M. Haider, P. R. Barker, N. W. Alcock, Z. Pikramenou, M. J., Hannon, D. G. Kurth, Angew. *Chem. Int. Ed.* 40 (2001) 3862-3865 for the compound AIM2.

In particular, the synthesis of the compound(s) according to the invention can be done according to the method described below.

The terpyridine ligands required for the synthesis of the organometallic compounds according to the invention have been prepared by using the Kröhnke reaction between 2-acetylpyridine and a suitable aryl-aldehyde compound in the presence of ammoniac.

For example, the homoleptic complexes AIM1, AIM2 and AIM3 are obtained with a respective yield of 90, 69 and 83% by making the suitable terpyridine ligand react (2 equivalents) with $FeCl_2$ in acetonitrile (diagram 1).

Diagram 1

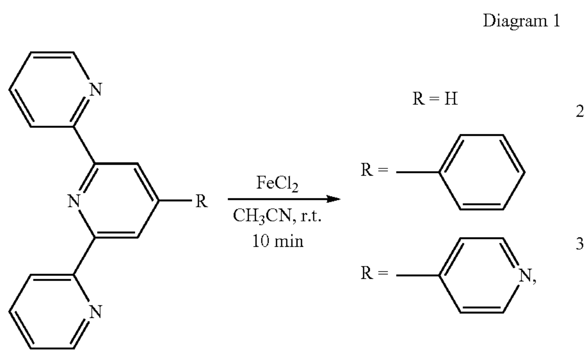

In particular, a solution comprising $FeCl_2$ (106 mg, 0.84 mmoles) and methanol (20 mL) is added to a solution comprising the suitable terpyridine ligand (1.68 mmoles) and methanol (20 mL). The mixture is thus stirred for 10 min. Ethyl ether (100 mL) is then added, leading to a purple solid collected by filtration, washed with ether and dried under vacuum.

AIM1. Yield: 90%. NMR $^1H$ (200 MHz, $CD_3OD$): δ=7.85 (d, J=8.1 Hz, 4H), 7.49 (t, J=8.2 Hz, 2H), 7.41 (d, J=8.2 Hz, 4H), 6.68 (m, 4H), 5.90 (d, J=3.8 Hz, 8H) ppm. HRMS (ESI) calcd for $C_{30}H_{22}FeN_6Cl_2$ m/z=261.0627 $[M-2\ Cl]^{2+}$. Found: 261.0683.

AIM2. Yield: 69%. NMR $^1H$ (200 MHz, DMSO-d6) 9.70 (s, 4H), 9.09 (d, J=8.5 Hz, 4H), 8.57 (d, J=7.4 Hz, 2H), 8.05 (t, J=7.4 Hz, 4H), 7.85 (t, J=7.2 Hz, 4H), 7.78 (t, J=7.0 Hz, 2H), 7.3 (d, J=5.1 Hz, 4H), 7.2 (t, J=6.3 Hz, 4H). HRMS (ESI) calcd for $C_{42}H_{30}FeN_6Cl_2$ m/z=337.0936 $[M-2\ Cl]^{2+}$. Found: 337.0902.

AIM3. Yield: 83%. NMR $^1H$ (200 MHz, $CD_3CN$): δ=9.27 (s, 2H), 9.08 (d, J=5.8 Hz, 2H), 8.65 (d, J=8.1 Hz, 2H), 8.38 (d, J=5.8 Hz, 2H), 7.97 (dt, J=6.7 Hz, 1.2 Hz, 2H), 7.22-7.10 (m, 4H) ppm. HRMS (ESI) calcd for $C_{40}H_{28}FeN_8Cl_2$ m/z=338.0888 $[M-2\ Cl]^{2+}$. Found: 338.0906.

II. Therapeutic Use of the Compound(s) of General Formula (I)

As has already been mentioned above, the organometallic compound(s) of formula (I) according to the invention having a DNA-demethylating action can also represent an active substance for therapeutic purposes, as will be described below.

The present invention is thus based on an organometallic compound comprising an iron atom bound to two terpyridine groups, having a general formula (I) such as defined above for use as medicine.

Of course, the features described above for the organometallic compound(s) of formula (I) for non-therapeutic use are covered here for therapeutic use (namely for use as medicine).

In particular, according to an embodiment of the invention, the organometallic compound of formula (I) excludes the compound(s) where $R^1$=$R^3$=$R^4$=$R^6$=H and where $R^2$=$R^5$ is chosen from among an aromatic cycle of formula (V) or (VI), wherein Z is a sulphur atom or an aromatic cycle of formula (II) or (III) with Y=CH.

Preferably, the organometallic compound(s) according to the invention can be used in order to treat diseases linked to a cell hyperproliferation, particularly cancers.

In particular, the organometallic compound(s) according to the invention can be used to treat glioblastomas, promyelocytic leukaemia, prostate, ovarian, lung, breast, digestive tract cancers, particularly liver, pancreatic, head and neck, colon cancers, non-Hodgkin's lymphomas or melanomas, etc.

The compounds of the invention have an antiproliferative effect regarding tumour and blood cells. These compounds lead to an accumulation of G2/M or G0/G1 phase cells. A cell death can be observed, but only after long treatments of a minimum of 96 h. Thus, these compounds can be used in order to reduce the tumour proliferation.

Furthermore, the organometallic compound(s) can be used to treat tumours that are resistant to other anticancer agents.

By the demethylating capacity of these compounds, the Applicant has also discovered that the organometallic compound(s) according to the invention could be used to treat other diseases linked to a deregulation of epigenetic modifications, such as to treat inflammation, obesity, neurodegenerative diseases or cardiovascular diseases.

Also, the present invention can be intended to form a pharmaceutical composition comprising, in a pharmaceutically acceptable carrier, at least one organometallic compound of formula (I) such as defined above.

Of course, the features described above for the organometallic compound(s) of formula (I) for non-therapeutic use or for use as medicine are covered here for therapeutic use as medicine.

In the context of the invention, the term "pharmaceutically acceptable carrier" refers to substances such as excipients, vehicles, additives, buffers which are conventionally used, in combination with one or more of the active ingredients (here, the organometallic compound(s) according to the invention), for the preparation of a medicine. The choice of such carriers mainly depends on the route of administration considered.

Generally, the pharmaceutically acceptable carrier is an excipient, a vehicle and/or an additive chosen from the group constituted by excipients, vehicles and/or pharmaceutically acceptable additives.

Techniques for preparing pharmaceutical compositions can be easily found by a person skilled in the art, for example, in the work, *Remmington's Pharmaceutical Sciences, Mid. Publis. Co, Easton, PA, USA*.

Physiologically acceptable additives, vehicles and excipients are also described in the work entitled, "*Handbook of Pharmaceutical Excipients, second edition, American Pharmaceutical Association,* 1994".

To formulate a pharmaceutical composition, a person skilled in the art can advantageously refer to the latest edition of the European Pharmacopeia or the U.S. Pharmacopeia (USP).

A person skilled in the art can in particular advantageously refer to the fourth edition 2002 of the *European Pharmacopeia* or also the edition USP 25-NF 20 of the *U.S. Pharmacopeia.*

Thus, the pharmaceutical composition can comprise one or more agents or vehicles chosen from among dispersants, solubilisers, stabilisers, preservatives, etc.

The pharmaceutical composition can be a human or veterinary pharmaceutical composition.

The pharmaceutical composition can be presented in a liquid form, or, preferably, in a solid form.

For an oral administration, a solid pharmaceutical composition will be preferred, for example in the form of tablets, pills or capsules.

In liquid form, a pharmaceutical composition will be preferred in the form of an aqueous suspension.

A pharmaceutical composition can thus be presented in a form for oral administration, by inhalation, parenteral or injection like, for example, intravenously, intramuscularly, subcutaneously, transdermally, intraarterially, etc.

According to a first aspect, the oral forms are particularly preferred.

According to a second aspect, the intravenous, intramuscular, subcutaneous routes and by inhalation are preferred.

As an example, for injections, the compositions are generally in the form of liquid suspensions, which can be injected by means of syringes or perfusions, for example. In this regard, the compounds are generally dissolved in an acceptable carrier which comprises saline, physiological, isotonic, buffered solutions, etc., compatible with a pharmaceutical use and known to a person skilled in the art. Agents or vehicles which can be used in liquid and/or injectable formulations are in particular methylcellulose, hydroxymethylcellulose, carboxymethylcellulose, polysorbate 80, mannitol, gelatine, lactose, vegetable oils, acacia, etc.

It is understood that the injection flow and/or the dose injected can be adapted by a person skilled in the art according to the patient, the pathology in question, the method of administration, etc.

Typically, the organometallic compound(s) according to the invention are administered to doses which could vary between 0.1 μg and 100 mg/kg of body weight, more generally between 0.01 and 10 mg/kg, typically between 0.1 and 10 mg/kg. Furthermore, repeated injections can be done. On the other hand, for chronic treatments, extended and/or delayed release systems can be advantageous.

As an example, for an oral administration, solid pharmaceutical forms as a pharmaceutical carrier can comprise, as vehicles, additives or excipients, at least one diluting agent, a flavour, a solubilising agent, a lubricating agent, a suspension agent, a disintegrating agent and an encapsulation agent, the identity and the function of these different conventions being documented completely in the *European Pharmacopeia* or in the *U.S. Pharmacopeia*, (USP).

Such compounds are, for example, magnesium carbonate, magnesium stearate, talc, lactose, pectin, dextrin, starch, gelatine, cellulosic materials, etc. The compositions in liquid form can also comprise water, if necessary mixed with propyleneglycol or polyethyleneglycol, and possibly also colouring agents, flavours, stabilisers and thickening agents.

Generally, in order to treat a patient of a pathology linked to a deregulation of the epigenetic modifications (such as cancer), the method comprises a step during which a therapeutically effective quantity of a purified dry extract of the organometallic compound(s) according to the invention, or the pharmaceutical composition described above is administered to said patient.

In the context of the invention, the term "treatment" refers to the preventive, curative, palliative treatment, as well as looking after patients (reducing suffering, improving lifespan, slowing down the progression of the disease, reducing the tumour growth, etc.). The treatment can furthermore be carried out in combination with other chemical or physical agents or treatments (chemotherapy, radiotherapy, gene therapy, etc.). The treatments and medicines of the invention are all particularly intended for humans.

Thus, the organometallic compound(s) according to the invention and/or the pharmaceutical composition can, for example, be used in the treatment of cancers in combination with an anticancer treatment implementing radiation, such as radiotherapy.

Also, the organometallic compound(s) according to the invention and/or the pharmaceutical composition can, for example, be used in the treatment of cancers in combination with at least one other anticancer chemical agent, conditioned and administered in a combined manner, separate or sequential. For example, it would be possible to provide a pre-treatment with a compound according to the invention, followed by a treatment with an anticancer agent.

The other anticancer chemical agent can be, for example, cisplatin, carboplatin, taxotere, taxol, tamoxifen, doxorubicin or 5-fluorouracile and is advantageously taxol, 5-fluorouracile or also tamoxifen or doxorubicin.

The Applicant has indeed surprisingly highlighted that the compounds according to the invention would make it possible to sensitise cancer cells to anticancer agents, even to act in synergy with them (examples 11 and 12).

The present invention thus makes it possible to inhibit in vivo, in vitro or ex vivo the proliferation of tumour cells, comprising the putting into contact of said tumour cells with the pharmaceutical composition. The tumour cells can be in particular those of the pathologies specified above.

Figure 2A:
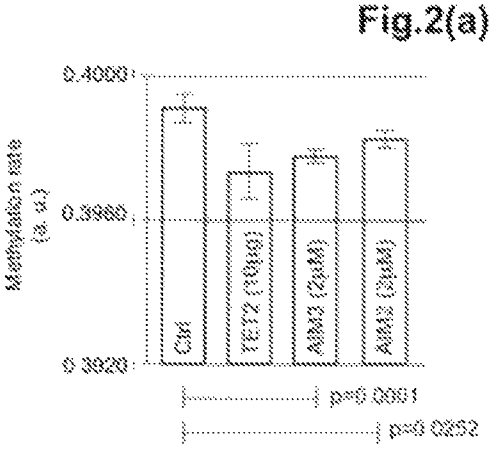
Figure 2B:
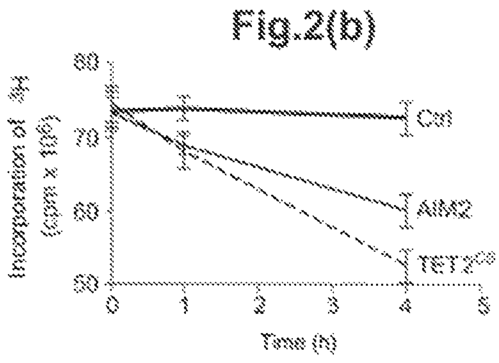
Figure 3:
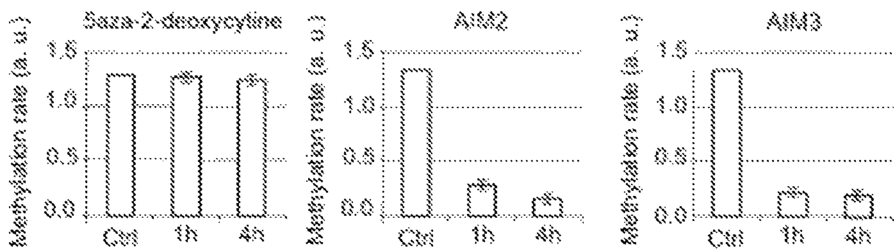
Figure 4:
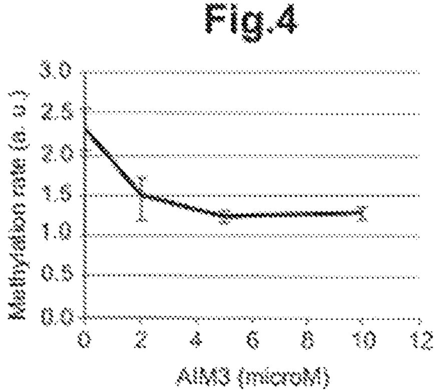
Figure 5:
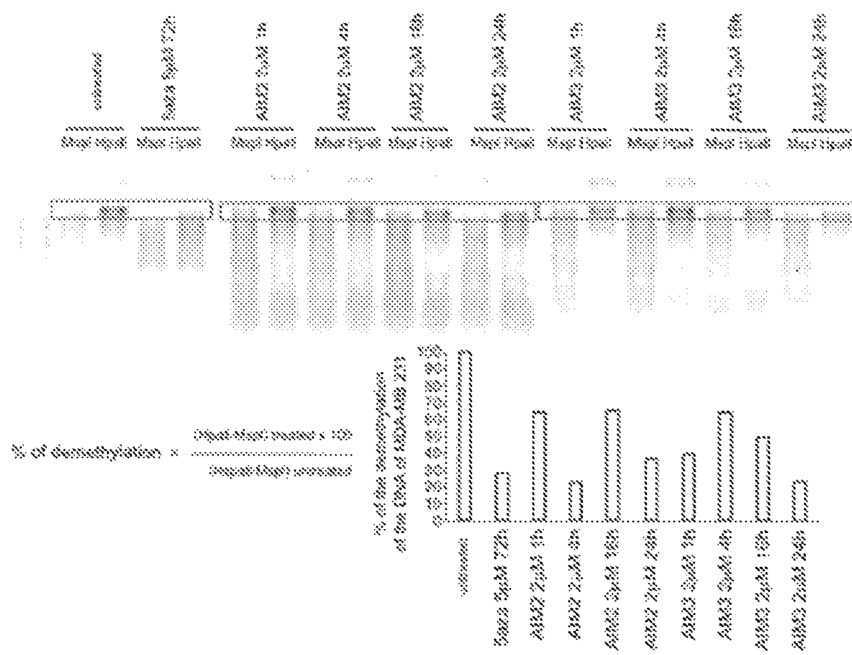
Figure 7:
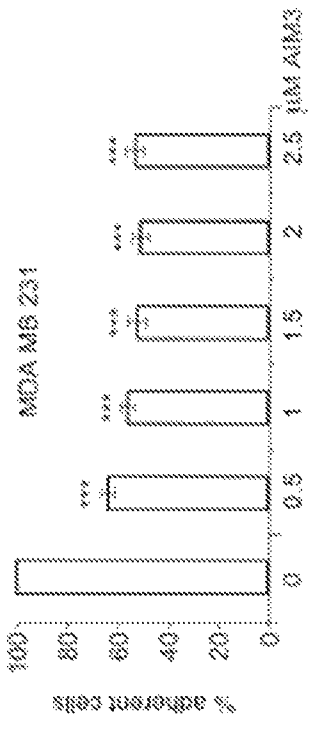
Figure 7:
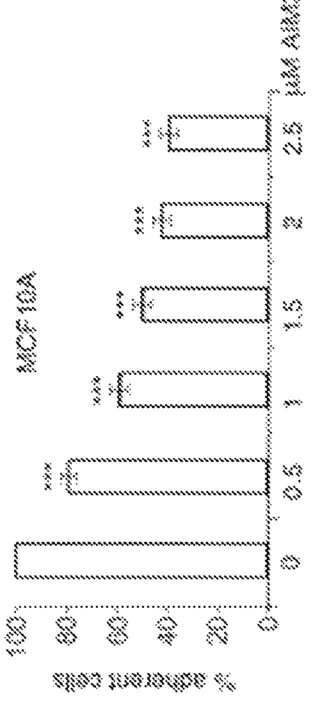
Figure 7:
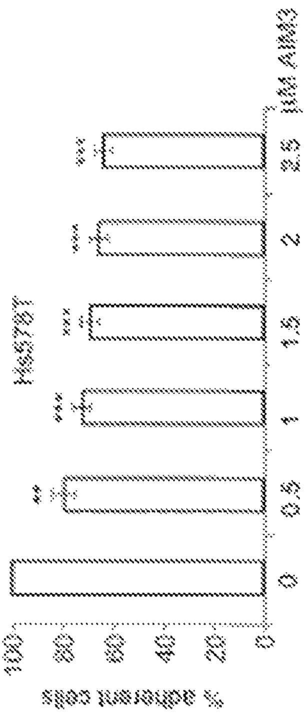
Figure 8:
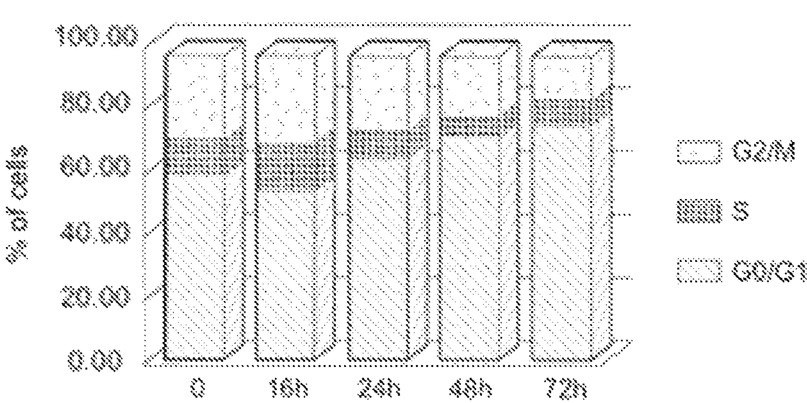
Figure 8:
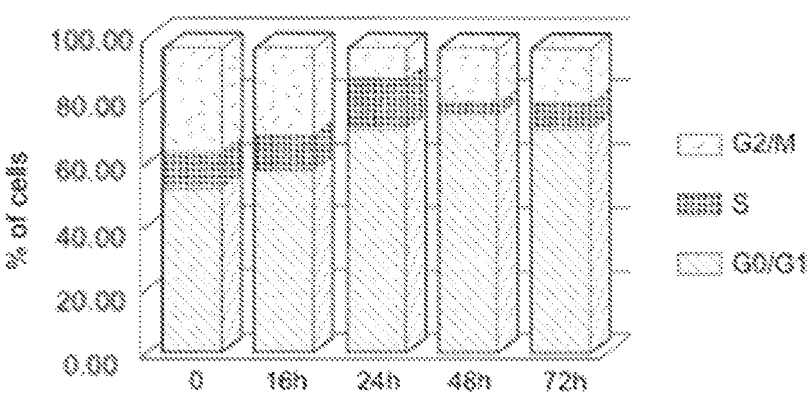
Figure 9:
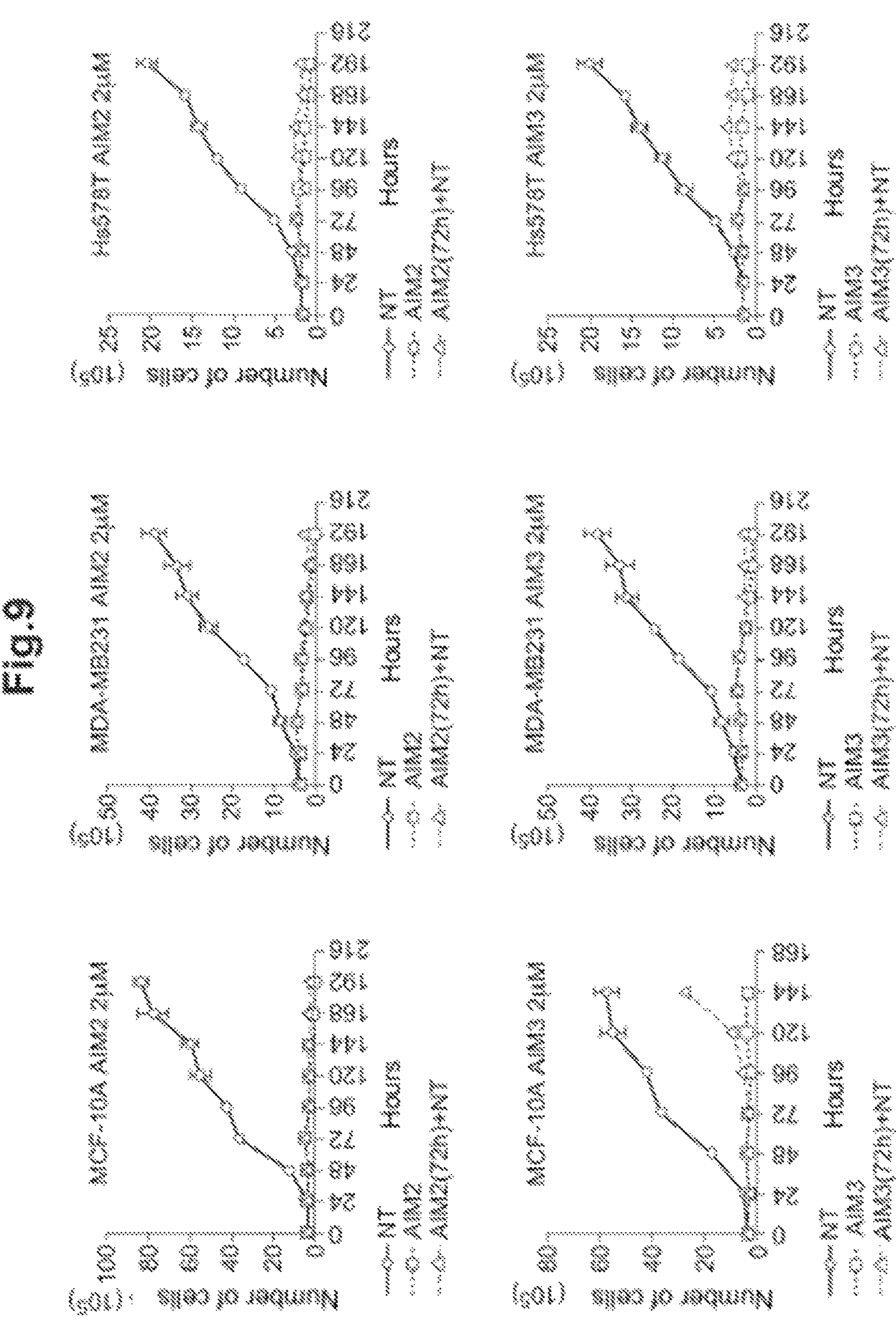
Figure 10:
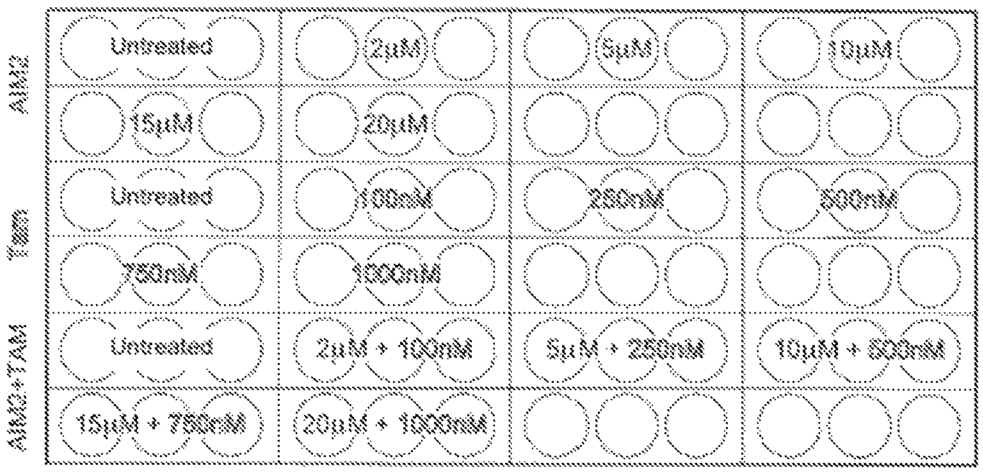
Figure 11:
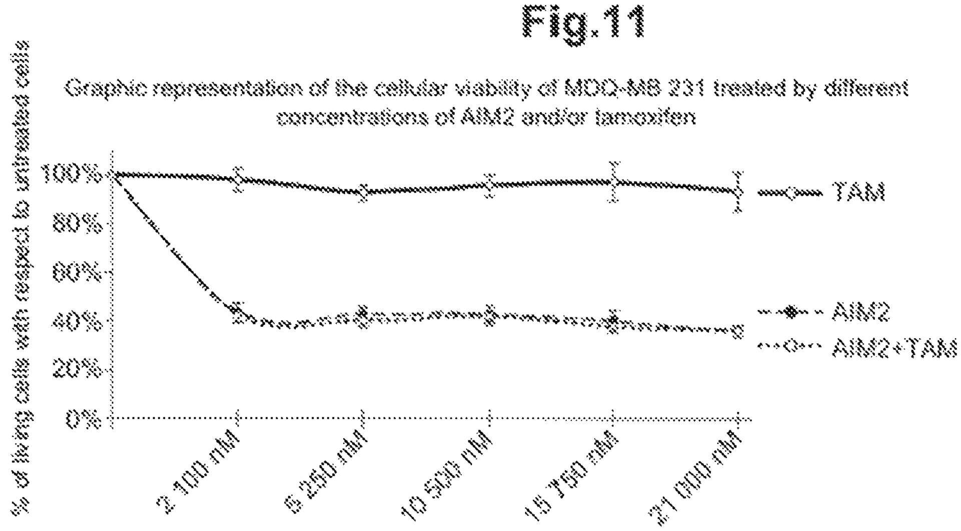
Figure 12:
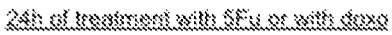
Figure 12:
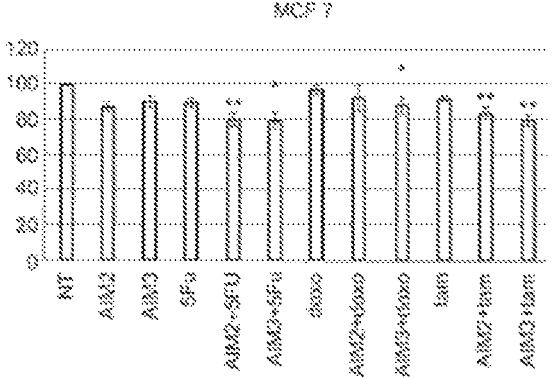
Figure 12:
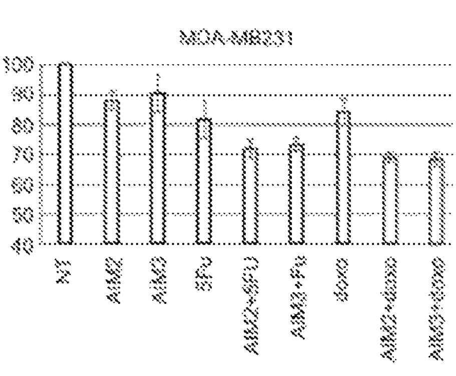
Figure 12:
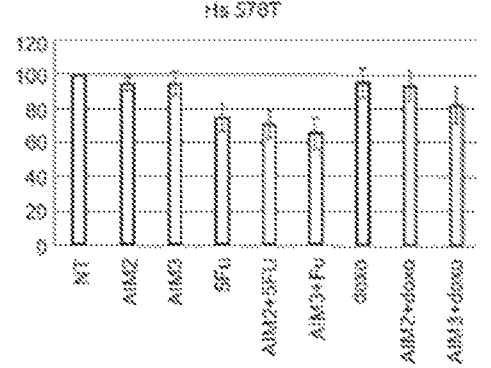
Figure 12:
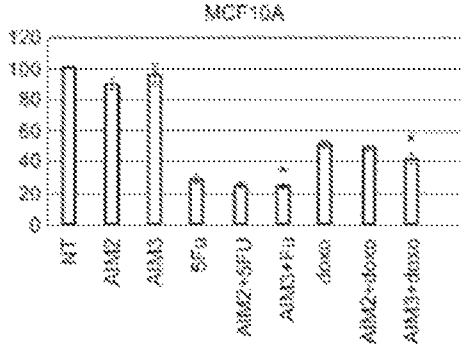
Figure 12:
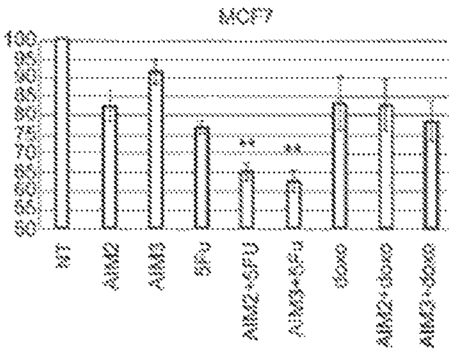
Figures 13, 14:
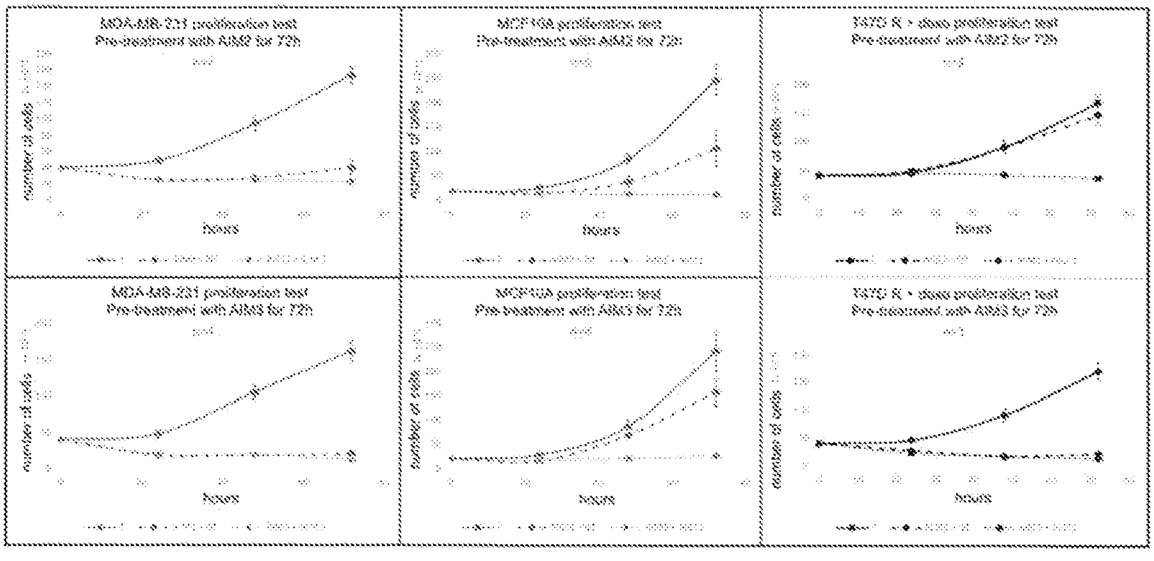
Figure 15:
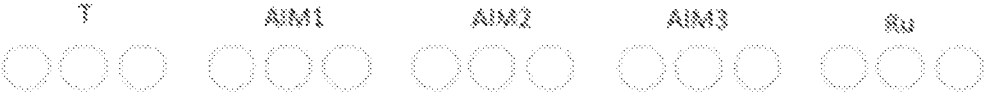
Figure 16:
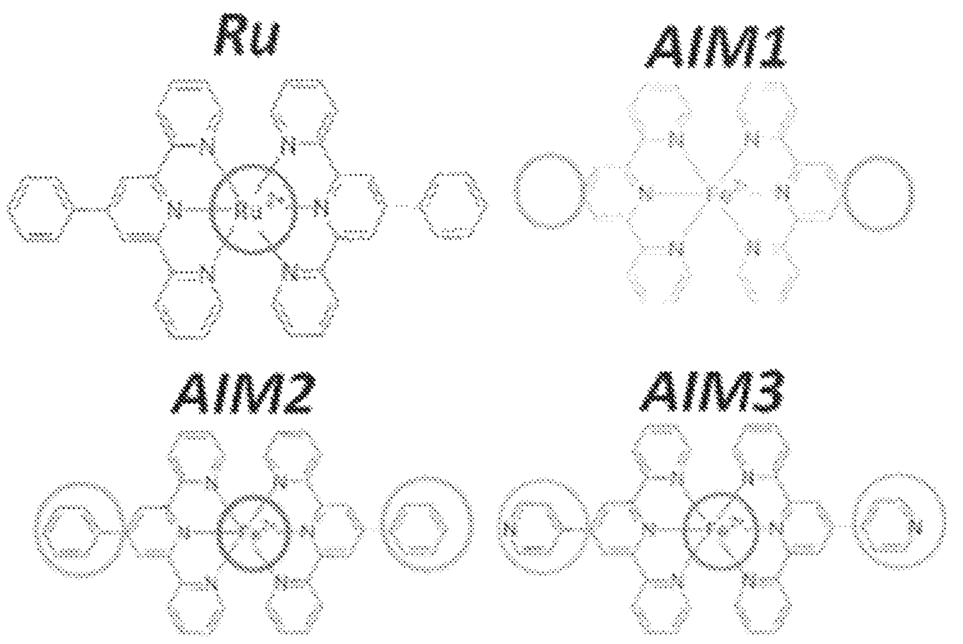
Figure 17:
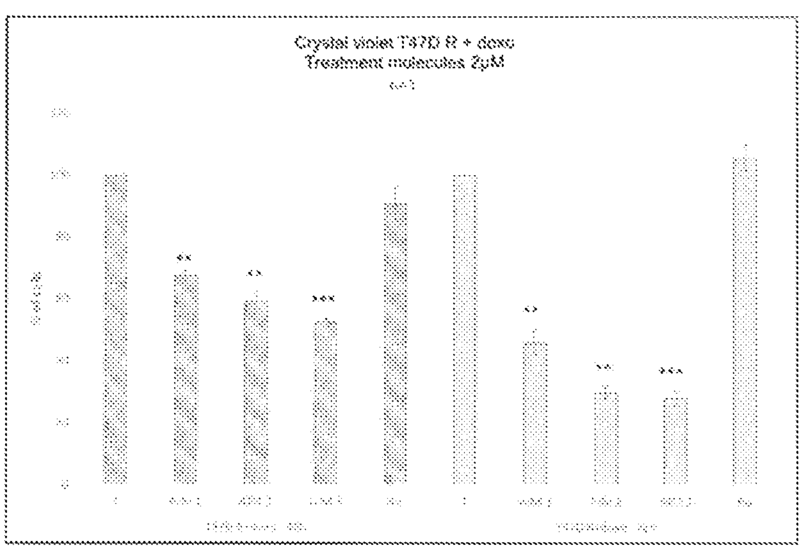
Figure 18:
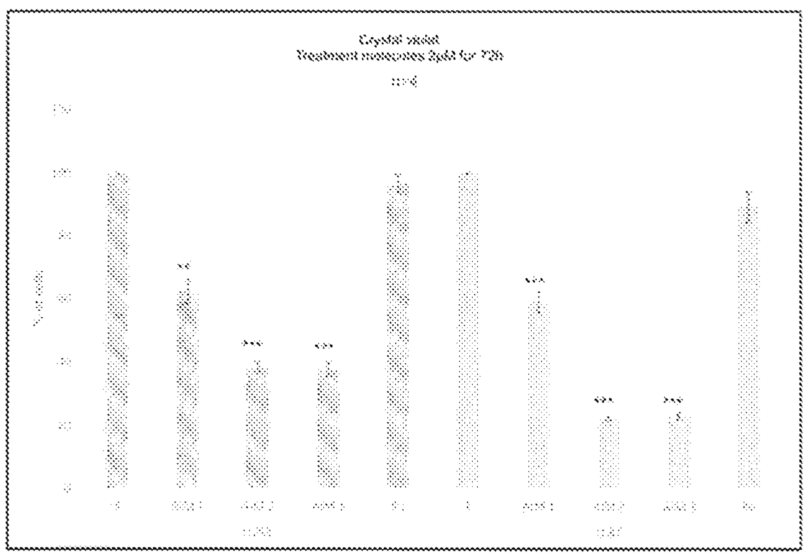
Figure 19:
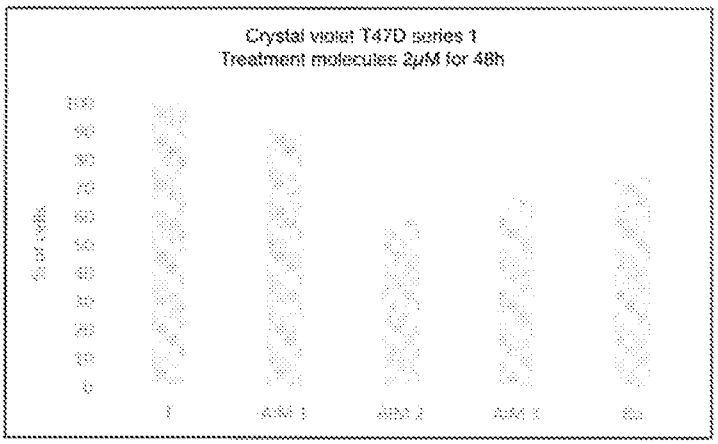
Figure 20:
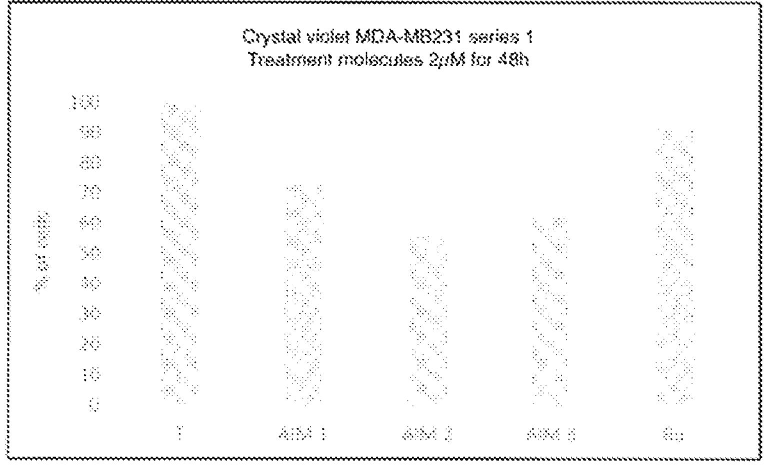

The invention is furthermore illustrated, without for all that being limited, by the appended figures and the following examples where:

FIG. 1: represents the result of an experiment of molecular modelling of the demethylating capacity of the compound AIM3 according to the invention;

FIG. 2: represents the evaluation of the demethylating power of the compounds AIM2 and AIM3 according to the invention in an in vitro system, (a) ELISA tests have been carried out in order to measure the rate of methylated cytosines present on a DNA fragment after action of the demethylase TET2 or molecules AIM2 and AIM3; (b) the demethylating activity of AIM2 (2 μM) and of the his-tagged-TET2 protein (10 μg) has been measured by a dosing of the incorporation of methyl groups radiomarked at the level of a biotynil double-strand DNA and previously methylated by the MSsl enzyme;

FIG. 3: represents the evaluation of the overall demethylating power of the molecules AIM2 and AIM3 in the cells U251: an ELISA test has been carried out in order to measure the rate of methylated cytosines present at the level of the DNA of untreated U251 cells versus treated for 1 or 4 h with 2 μM of 5aza-2-deoxycytidine, AIM2 or AIM3;

FIG. 4: represents the evaluation of the overall demethylating power of the molecule AIM3 on T98G cells and shows the absence of dose effect of the demethylating power of the molecule AIM3 following the incubation thereof for 1 h ($p=0.2578$);

FIG. 5: represents the evaluation of the overall demethylating power of the molecules AIM2 and AIM3 according to the invention on MDA-MB231 cells: a quantification by densitometry has made it possible to obtain a quantitative value of the intensity of bands have in the framed part of the gel (the calculation of the percentage of demethylation has been calculated using the formula indicated);

FIG. 6: represents the impact of the molecule AIM2 according to the invention on the proliferation of MCF-10A mammary epithelial cells and MDA-MB231 and Hs578T mammary tumour cells: the cells have been seeded, after 24 h of culture, the cells have been treated for 48 h with variable concentrations of the molecule AIIM2; the determination of the number of adherent cells has been done by a crystal violet coloration and quantified by measuring the absorbance at 595 nm; the results correspond to the mean of 4 independent experiments, standard error means (SEM) are indicated and the significance of the data has been calculated by comparing the treated vs untreated cells (Student test);

FIG. 7: represents the impact of the molecule AIM3 according to the invention on the proliferation of MCF-10A mammary epithelial cells and MDA-MB231 and Hs578T mammary tumour cells: the cells have been seeded, after 24 h of culture, the cells have been treated for 48 h with variable concentrations of the molecule AIIM3; the determination of the number of adherent cells has been done by a crystal violet coloration and quantified by measuring the absorbance at 595 nm; the results correspond to the mean of 4 independent experiments, the standard error means (SEM) are indicated—the significance of the data has been calculated by comparing the treated vs untreated cells (Student test);

FIG. 8: is an analysis of the cell cycle of the MCF-10A cells, treated or not with 0.5 μM of AIM2 or AIM3; the cells have been seeded and treated with 0.5 μM of AIM2 or of AIM3 for 0, 16, 24, 48 and 72 h; after detachment, the cells are fixed and permeabilised in a 70% cold ethanol solution; a marking with propidium iodide is then done in order to mark the DNA and the fluorescence is quantified by flow cytometry;

FIG. 9: represents an analysis of the number of cells, treated or not with 2 μM of AIM2 or AIM3. The cells have been seeded and treated with 2 μM of AIM2 or of AIM3 for 0, 24, 48, 72, 96, 120, 144, 168 and 192 h. After detachment, the cells are counted using a counting cell of Malassez type. The medium of the NT or AIM2 or AIM3 cells is renewed every 72 h. For the cells AIM2(72)+NT or AIM3(72)+NT, the culture medium contains the molecule indicated only for 72 h and after that, it is replaced by a medium without molecule in order to test the reversibility of the effect;

FIG. 10: corresponds to the experiment plan of the plate of example 11;

FIG. 11: is a graphic representation of the cellular viability of MDA-MB 231 treated by different concentrations of the compound AIM2 according to the invention and/or tamoxifen;

FIG. 12: represents a set of graphics showing the sensitivity of different mammary tumour lines against the compounds AIM2, AIM3, conventional chemotherapy agents and the combinations thereof;

FIG. 13: represents the experiment plan of example 13;

FIG. 14: represents the inhibition of the proliferation by the molecules AIM2 and AIM3 which is reversible in certain cells; from left to right, the results are presented, relating to the MDA-MB-231 cells (triple negative mammary cancer cells), MCF10A cells (healthy mammary epithelial cells) and T47R+Doxo cells (mammary cancer cells that are resistant to doxorubicin) treated with AIM2 (panel at the top) or AIM3 (panel at the bottom) for 72 h of pre-treatment then re-seeded for an additional 72 h; the different conditions correspond to: T=without prior treatment nor during these 72 h; AIM2/3+NT cells pre-treated with AIM2 or AIM3 and then without treatment; AIM2/3+AIM2/3 cells pre-treated with AIM2 or AIM3 and then returned in the presence of AIM2 or AIM3 for 72 h;

FIG. 15: represents the experiment conditions of example 14;

FIG. 16: represents the molecules tested of example 14;

FIG. 17: represents the inhibition of the proliferation of T47D R+ doxo cells by the different molecules AIM1, AIM2, AIM3 and Ru after 48 and 72 h of treatment;

FIG. 18: represents the inhibition of the proliferation of the U251 and U87 glioblastoma cells by the different molecules AIM1, AIM2, AIM3 and Ru after 72 h of treatment;

FIG. 19: represents the inhibition of the proliferation of T47D cells by the different molecules AIM1, AIM2, AIM3 and Ru after 48 h of treatment; and FIG. 20: represents the inhibition of the proliferation of MDA-MB-231 cells by the different molecules AIM1, AIM2, AIM3 and Ru after 48 h of treatment.

III. EXAMPLES

In order to biologically confirm these data, a study of the impact of the molecules AIM3 and AIM2 on the methylation of the DNA has been carried out in acellular and cellular systems.

Example 1: Solubilisation of the Compounds AIM2 and AIM3 According to the Invention for Use on Cells For the different tests described below, the compounds AIM2 and AIM3 according to the invention have been solubilised beforehand as follows (Table 1):

TABLE 1

| Compound | Mother dilution | Daughter dilutions |
|---|---|---|
| AIM2 | 1 mM in PBS + 20% ethanol kept at 4° C. | done in PBS 1X and kept at 4° C. |
| AIM3 | 5 mM in PBS + 20% ethanol kept at 4° C. | done in PBS 1X and kept at 4° C. |

For the compound AIM2, the daughter solutions can precipitate at 4° C. It is thus necessary to incubate them at 37° C. for 10 min before the use thereof.

Example 2: Molecular Modelling of the Demethylating Capacity of the Compound AIM3 According to the Invention In order to demonstrate the demethylating action of the organometallic compounds according to the invention, the Applicant has carried out a molecular modelling of the demethylating capacity of the compound AIM3 according to the invention.

To this end, the energy profile linked to the demethylation reaction has been made using quantic chemistry calculations. In particular, a model system comprising a methylated cytosine and AIM3 has been used. The geometries of the reagents and of the products have been optimised using density functional theory ("DFT"), by using wB97XD as exchange-correlation function and LANL2DZ as orbital base.

Subsequently, the transition state, i.e. the maximum energy conformation, has also been optimised which has made it possible to estimate the energy barrier which must be surmounted to be able to complete the demethylation reaction, in this case. The energy profile of the reaction in the space connecting the reagents and the products via the transition state has also been estimated by analysing the energy variation according to a reaction coordinate, i.e. the distance between the methyl and the peripheral nitrogen of AIM3. The effects of the solvent, water, have been considered using a polarisable continuum model ("PCM").

All the molecular modelling calculations have been made via the Gaussian 09 version D01 software and thanks to the standard molecular modelling techniques, detailed in particular in numerous works, like for example, "Chris J. Cramer Essential of Computational Chemistry Wiley eds". In addition, a person skilled in the art can refer to the Gaussian 09 manual for a detailed illustration of geometry optimisation techniques which have been used.

As FIG. 1 shows, the results obtained have revealed that the compound AIM3 and the other organometallic compounds of formula (I) could lead to a direct DNA demethylation via favourable thermodynamic reactions.

Example 3: Measuring the Rate of 5-Methylacytosine (5mC) by ELISA (FIG. 2 (*a*))

Acellular Test:

Acellular experiments consist of incubating the methylated DNA (Qiagen, France) at 37° C. for 1 h with either 2 μM of molecules AIM2 and AIM3, or with the TET2 recombinant protein which is a protein known for the demethylating role thereof and serving as a positive control or with water (Ctrl).

In particular, the methylated DNA (500 ng, ref #N4007 NEB, genomic DNA of HeLa cell hypermethylated in vitro by the M.Sssl enzyme) is incubated for 1 h at 37° C. either in the presence of water (Ctrl), or in the presence of AIM2 (2 μM) or AIM3 (2 μM), or in the presence of 10 μg of his-tagged-TET2 protein.

The DNA is then used to carry out a 5mC-ELISA test (Zymo Research), i.e. making it possible to measure the level of 5-methylcytosines (see below).

Cellular Test:

U251 glioma cells or T98G glioblastoma cells have been seeded at $2.10^6$ respectively. 24 h after seeding, the cells have been treated for 1 or 4 h with the molecules AIM2 or AIM3 at a rate of 0, 2, 5, 10 μM. After the treatment, the culture medium is replaced by a medium without molecules and the cells are kept for 48 h in culture. The cells are then detached mechanically with a scraper in order to carry out an total DNA extraction via the use of the QiaCube automaton (Qiagen) and of the QIAamp DNA Mini QIAcube Kit (Qiagen), without modification with the instructions provided by Qiagen.

5mC-ELISA (Zymo Research)

The DNA (100 ng) collected as indicated above is first denatured at 98° C. for 5 min (use of the MyCycler BioRad thermocycler), before being deposited in plate wells: 96 wells provided for this purpose (5mC-ELISA kit, Zymo) for 1 h of incubation at 37° C. The supernatant is then removed and the wells are washed 3 times with 200 μL of washing buffer (provided by the kit). Then, 200 μL of washing buffer are incubated in each well for 30 min at 37° C. The step of revealing/quantifying the 5-methylcytosines is carried out with the incubation (1 h, 37° C.) of the anti-5mC antibody provided by the kit (ref/A3001-30), diluted to 1/2000. After 3 washes (200 μL of washing buffer provided by the kit), the primary antibody is revealed following the incubation (1 h, 37° C.) of the HRP coupled secondary antibody (D5325-3-30). Finally, after 3 washes (200 μL of washing buffer provided by the kit), the revelation of the ELISA is done by adding 100 μL of "HRP developer" (provided by the kit). The reading of the ELISA plate is done at 405-450 nm (Victor plate reader, Perkin Elmer). In parallel, a standard range is achieved with the methylated DNA, of which the percentage of 5mC is known (range: 0, 5, 10, 25, 50, 75, 100%).

As FIG. 2(*a*) shows, measuring the methylcytosine rate (ELISA test) present at the level of the DNA probe has made it possible to reveal a significant drop in methylcytosines after a treatment with the molecules AIM3 and AIM2.

Example 4: Dosing of Radiomarked Methyl Groups (FIG. 2(*b*))

In addition, the demethylating activity of AIM2 (2 μM) and the his-tagged-TET2 protein (10 μg) (positive control) has been measured by a dosing of the incorporation of radiomarked methyl groups at the level of a biotynil double-strand DNA and previously methylated by the M.SSs1 enzyme.

Protocol

This DMB experiment is carried out as described by Yokochi and Robertson (2004).

A 96-well plate is previously pre-treated with 10 mg/ml of BSA (bovine serum albumin) for 30 min.

The magnetic beads (10 mg/ml, Dynal) are washed three times with the TENT2M buffer (20 mM Tris, pH 8.0, 2 mM EDTA, 0.01% Triton X-100, 2 M NaCl). The concentration of these beads is adjusted to 2.5 mg/ml with the TENT2M buffer and 1/10 of the volume with the non-radioactive AdoMet form (100 mg/ml; Sigma).

The methylation reaction (40 μl) contains 200 U of the M.Sssl enzyme (NEB #M0226) 125 nM of DNA oligonucleotides, 200 ng of DNA, and 900 nM tritium-labelled AdoMet (Amersham Bioscience, 1 mCi/ml) in the reactional medium (50 mM Tris, pH 8.0, 5 mM EDTA, 10% glycerol, 10 mM 2-mercaptoethanol, 0.5 mM of phenylmethylsulphonyl fluoride).

After an incubation of 30 min at 37° C., the reactions are stopped by the addition of an equivalent volume of magnetic beads in suspension and a gentle stirring for 15 min at ambient temperature. The magnetic beads are separated using a magnet and washed successively with 300, 200, 150, and 100 μl TENT1M (10 mM Tris, pH 8.0, 1 mM EDTA, 0.005% Triton X-100, 1 M NaCl). The magnetic beads are resuspended in 25 μl of TENT1M in the presence of "putative demethylating agents" or with 100 μg of nuclear extract isolated using the kit, nuclear extract kit (Active Motif, #40410). After the incubations, the magnetic beads are separated using a magnet and washed successively with 300, 200, 150, and 100 μl of TENT1M (10 mM Tris, pH 8.0, 1 mM EDTA, 0.005% Triton X-100, 1 M NaCl). Then, the tritium rate incorporated is measured in a scintillation counter.

Results (FIG. 2(*b*))

As FIG. 2(*b*) shows, the compound AIM2 has a DNA-demethylating action.

Example 5: Experiment on U251 Glioblastoma Cells (FIG. 3)

At the same time, with the aim of verifying the demethylating power of these organometallic molecules according to the invention, experiments on U251 glioblastoma cells have been carried out.

Protocol

The experiment carried out on the U251 cells has consisted of treating the latter for 1 or 4 h with 2 μM of AIM2, AIM3 or of 5aza-2-deoxycytidine which is a demethylating agent known and commonly used.

Following the treatments, the DNA has been extracted and subjected to an ELISA test in order to determine the methylated cytosine rate (protocol, see EXAMPLE 3).

Result:

As indicated in FIG. 3, the molecules AIM2 and AIM3 have a demethylating power after 1 h and 4 h of incubation clearly greater than that of 5aza-2-deoxycytidine which is the demethylating agent known and commonly used, but which requires an incorporation within the DNA.

Example 6: Experiment on Another T98G Glioblastoma Cell Line (FIG. 4)

Moreover, the demethylating action of AIM3 has also been observed on another glioblastoma cell line, called T98G (FIG. 4).

Protocol

The experiment carried out on the T98G cells has consisted of treating the latter for 1 h with different concentrations of the compound AIM3 according to the invention, namely 0; 2; 5 and 10 μM.

Following the treatments, the DNA has been extracted and subjected to an ELISA test in order to determine the methylated cytosine rate (protocol, see EXAMPLE 3).

Results:

As indicated in FIG. 4, in these cells, the demethylating power of the molecule AIM3 is visible after 1 h of treatment at a concentration of 2 μM. However, an increase of the concentration of this molecule (of the order of 5 to 10 μM) does not increase the demethylating power thereof. Indeed, a 2 μM dose of AIM3 has a demethylating effect which is similar to that of a 10 μM dose of AIM3.

Example 7: Experiment on MDA-MB231 Cells (FIG. 5)

An enzymatic digestion experiment has also been carried out in order to determine the overall demethylation percentage induced by the molecules AIM2 and AIM3 according to the invention.

Protocol

1. Cell Culture 1.1. Conditions of Culture and Treatments

The cells of the MDA-MB 231 mammary cancer line are cultivated in an RPMI 1640 (Gibco) medium containing 2 mM of L-Glutamine (Sigma), 0.1 mg/mL of gentamicin (Sigma) and 10% of foetal bovine serum (Sigma) decomplemented for 30 minutes at 56° C. They are incubated at 37° C. and at 5% of $CO_2$.

The seeding is done in 6 cm Petri dishes (4 mL medium/dish) according to the following conditions (table 2):

TABLE 2

| | | |
|---|---|---|
| Untreated | | $4.10^5$ cells |
| AIM2 2 μM | 1 h | |
| | 4 h | |
| | 16 h | |
| | 24 h | |
| AIM3 2 μM | 1 h | |
| | 4 h | |
| | 16 h | |
| | 24 h | |
| 5aza2déoxycytidine 5 μM 72 h | | $8.10^5$ cells |

1.2. Conditions for Returning Molecules

5aza2deoxycytidine (Sigma A3656)

The powder is returned at 100 mM in DMSO (Sigma). This stock solution is aliquoted (2 μL) and stored at −80° C.

The intermediate dilutions are done in the culture medium.

AIM2

The powder (717.07 g/mol) is returned at 1 mM in PBS (Fisher) containing 20% of ethanol. This mother solution is stored at 4° C.

The intermediate dilutions are done in PBS.

AIM3

The powder (719.06 g/mol) is returned at 5 mM in PBS containing 20% of ethanol. This mother solution is stored at 4° C.

The intermediate dilutions are done in PBS.

NB: The mother solutions of AIM2 and AIM3 precipitate at 4° C. It suffices to incubate them for 5 minutes at 37° C. in order to resolubilise them.

1.3. Cell Harvesting Procedure

The cell layer is washed with 2 mL of PBS, then trypsinated with 0.5 mL of trypsin EDTA 1× (Sigma) for 5 minutes at 37° C. The action of the trypsin is then inhibited by adding 4 mL of culture medium.

The cell suspension is finally centrifuged at 200G for 5 minutes and the button kept at −20° C.

1.4. Plan

TABLE 3

| D1 | D2 | D3 | D4 | D5 |
|---|---|---|---|---|
| Seeding | | | | at X-5 h:<br>Cell harvest<br>On dishes for 16 h<br>at X-4 h:<br>Treatment AIM2/3<br>2 μm<br>On dishes for 4 h<br>at X-1 h:<br>Treatment AIM2/3<br>2 μm<br>On dishes for 1 h |

TABLE 3-continued

| D1 | D2 | D3 | D4 | D5 |
|---|---|---|---|---|
| | at X h:<br>Treatment<br>5 aza 5 μM | at X h:<br>Renew medium<br>5 aza | at X h:<br>Renew medium<br>5 aza<br><br>Treatment<br>AIM2/3<br>2 μM on dishes<br>for 24 h<br>at X h:<br>Treatment<br>5 aza 5 μM | at X h:<br>Cell harvest on<br>untreated dishes<br>for 1 h, 4 h and 24 h |

2. Lysis and Extraction of the DNA 2.1. Cell Lysis

Each button is returned in 100 μL of PBS, to which are added in order:

100 μL of water

150 μL of SDS 0.1%

50 μL of Proteinase K at 10 mg/mL (Sigma)

The lysis is done at 37° C. for the whole night.

2.2. Extraction of the DNA

Add to the lysate 2 volumes of phenol/chloroform 5:1

Vortex for 30 seconds

Centrifuge at 16000G for 5 minutes at ambient temperature

Recover the aqueous phase (supernatant)

Add 1 volume of chloroform/isoamylalcohol 23:1

Centrifuge at 16000G for 5 minutes at ambient temperature

Recover the aqueous phase (supernatant)

Add 1/10 of the volume of sodium acetate 3M

Then 1 volume of absolute cold ethanol

Vortex for 10 seconds

Leave to precipitate for one night at −20° C.

Centrifuge at 12000G for 15 minutes at 4° C.

Wash the button with 500 μL of ethanol 70%

Centrifuge at 12000G for 5 minutes at 4° C.

Leave the button to dry (cover of the open tube) until it becomes translucid

Dissolve the button in sterile water (around 100 μL volume to be adjusted according to the size of the button obtained)

Dose the DNA at 260 nm

Keep the DNA at −20° C.

3. Enzymatic Digestions with MSPI and HpaII (Fisher, ER0541 and ER0511)

1 μg of DNA of each condition is digested with MSPI and HpaII according to the following protocol:

2 μL Buffer TANGO 10λ

1 μg DNA

Water qsp 16 μL

2 μL HpaII or MspI (=20 U)

Incubate at 37° C. for the whole night, then 20 minutes at 80° C. (enzyme inactivation)

4. Migration of the DNA Digested on Agarose Gel

Add 4 μL of deposition blue 6× to each digestion volume (20 μL)

(Deposition blue 6×: 10 mM TrisHCl pH 7.6, 60 mM EDTA, 60% glycerol, 0.03% bromophenol blue, 0.03% xylene cyanol FF)

Make all of each digestion migrate on an agarose gel 1%+2 μL BET 10 mg/mL at 90V for 40 minutes.

The intensity of each strip is measured using the Quantity One software.

Calculation % of DNA methylation: $(HpaII-MspI)_{Treated}\times 100/(HpaII-MspI)_{Untreated}$ Results:

The data presented in FIG. 5 confirm that, like 5-azacytidine, the treatment of MDA-MB231 cells with the molecules AIM2 and AIM3 makes it possible to reduce the overall percentage of methylation of the genome.

Example 8: Impact of the Compounds AIM2 and AIM3 According to the Invention on the Proliferation of MCF-10A Mammary Epithelial Cells and MDA-MB231 and Hs578T Mammary Tumour Cells (FIG. 6 and FIG. 7)

Crystal Violet Protocol

TABLE 4

| 96-well plate seeding: | |
|---|---|
| MDA MB 231 cell line: | 10000 cells/well in<br>100 μL of culture medium |
| MCF10A cell line: | 2000 cells/well in<br>100 μL of culture medium |
| Hs578T cell line: | 5000 cells/well in<br>100 μL of culture medium |

The cells are seeded according to the densities indicated above (Table 4). After 24 h of culture, the culture medium is replaced by the medium containing or not, the molecules AIM2 or AIM3 to concentrations of 0.5; 1; 1.5; 2 and 2.5 μM in four specimens for 48 h. After these 48 h of treatment, the culture medium is removed and the cells are washed with a PBS 1× solution. They are then fixed in 100 μL of culture medium containing 4% of paraformaldehyde and incubated for 20 min at ambient temperature. The cells are then rinsed with a PBS 1× solution. Then, they are coloured for 30 min using 100 μL of the Crystal violet 0.1% solution (1/5 dilution in $H_2O$ of the stock solution: 0.5% crystal violet 2% ethanol). The cells are then washed 3 times with 100 μL of $H_2O$.

The following step consists of solubilising the crystal violet in order to obtain a coloured solution which can be dosed. Thus, 100 μL of an acetic acid solution at 10% is added, then the plates are incubated while stirring until a total solubilisation of the Crystal Violet. A reading of the absorbance is then made at 595 nm thanks to a plate reader (VICTOR).

Results:

At the biological level, it has been determined that the molecules AIM2 and AIM3 had an antiproliferative action on normal mammary epithelial cells (MCF-10A) and on mammary tumour cells (MDA-MB231 and Hs578T) (FIGS.

6 and 7). These results make it possible to define the inhibiting median concentration (1050) of the molecules AIM2 (FIG. 6) and AIM3 (FIG. 7). The 1050 of the molecule AIM2 in the MCF-10A cells is comprised between 0.5 and 1 μM and in the MDA-MB231 cells between 1 and 1.5 μM; the 1050 of the molecule AIM3 in the MCF-10A cells is comprised between 1 and 1.5 μM and in the MDA-MB231 cells between 1.5 and 2 μM.

Example 9: Impact of the Compounds AIM2 and AIM3 According to the Invention on the Proliferation of MCF-10A Mammary Epithelial Cells by Flow Cytometry (FIG. 8): Absence of Cell Toxicity With the aim of defining this antiproliferative action, a study of the cell cycle of the MCF-10A mammary epithelial cells by flow cytometry has also been carried out (FIG. 8).

Protocol: Cell Cycle

1. Seed the cells in 60 mm dishes.

The concentration of the cells is presented in the table below.

TABLE 5

| Cell line | Concentration (number/mL) |
|---|---|
| MCF-10A (0 h, 16 h, 24 h) | $1.5 \times 10^4$ |
| MCF-10A (48 h, 72 h) | $5 \times 10^4$ |
| MDA-MB231 | $1 \times 10^5$ |
| Hs578T | $5 \times 10^4$ |

2. Treat the cells according to the treatment time.
3. Recover the medium from each dish in a 15 ml tube.
4. Wash the cells with 2 mL of PBS.
5. Recover the PBS in the tube.
6. Add 1 mL of trypsin 1× in each dish and incubate them in the incubator for 5 minutes for the MDA-MB231 and the Hs578T, and 15 minutes for the MCF-10A.
7. Inhibit the trypsin with the medium and recover the cells in the tube.
8. Re-suspend the cells and count them using a TC10™ Automated Cell Counter (Bio-Rad).
9. Take $1\times10^6$ cells in another 15 ml tube, centrifuge at 500G for 5 minutes.
10. Suction the supernatant and wash the cells with 2 ml of PBS.
11. Centrifuge at 500G for 5 minutes.
12. Suction the supernatant, retake the button in 300 μL of PBS and separate the cells with a 200 μl pipette.
13. Add 700 μL of absolute cold ethanol drop by drop while vortexing it all in the tube.
14. Put the cells in the fridge at −20° C. at least 30 minutes to ensure a permeabilisation and a correct fixing.
15. Take 500 μL of cells ($5\times10^5$ cells) of each suspension and centrifuge at 800G for 10 minutes.
16. Suction the supernatant delicately.
17. Return each button in 500 μl of DNA staining solution containing 100 of RNase A and 2 μl of propidium iodide (IP, 50 μg/ml). The unmarked buttons are returned in 500 μL of PBS.
18. Incubation for 10 minutes in the dark.
19. Reading of the FACS.

Results:

As FIG. 8 shows, the results obtained indicate that a treatment with 0.5 μM of AIM2 and AIM3 induces a blocking of the cell cycle in phase G1. The absence of cells in phase subG1 indicates that these molecules do not have any cell toxicity under these treatment conditions.

Example 10: Impact on the Cell Proliferation (Cleaved PARP Test by Western Blot) (FIG. 9)

The absence of cell death has been confirmed by experiments during which the absence of cleaved PARP protein has been verified by Western Blot.

The effect of these molecules on the cell proliferation has also been evaluated according to the treatment time, and no longer the molecule dose used. The 2 μM dose, which is that capable of leading to a DNA demethylation, has been chosen.

Protocol:

The cells are seeded in 60 mm dishes due at a rate of 4 mL/dish on the 1st day at the concentration indicated in the table below.

TABLE 6

| Cell line | Concentration (number/ml) |
|---|---|
| MCF-10A | $8 \times 10^4$ |
| MDA-MB231 | $1 \times 10^5$ |
| Hs578T | $4.5 \times 10^4$ |

6 hours after the seeding thereof, the organometallic complexes AIM2 and AIM3 at 2 μM or the solvent (0.04% of ethanol) for the untreated cells are added in the culture medium. From the treatment time chosen, 24, 48, 72, 96, 120, 144 hours, the treated and untreated cells are detached by action of the trypsin. After inactivation of the trypsin with the culture medium containing 10% of foetal bovine serum, the cells are washed in PBS and counted after coloration with Trypan Blue in order to only count the living cells (a fraction of 10 μl of the suspension is mixed with 10 μL of Trypan Blue at 0.4% (Thermo Scientific). The counting of the cells is carried out using a Malassez counting cell (Marienfeld-Superior).

a). Prior to the treatment, the AIMs molecules are preheated in a heating unit (Thermo Scientific) at 37° C. while stirring for 10 minutes in order to guarantee a total solubilisation.

b). For treatments longer than 72 hours, the mediums are renewed every 72 hours with or without AIMs.

c). In the proliferation reversibility test (red curves in the figure), the treatment is stopped after 72 hours, and the mediums are renewed without adding AIMs molecules.

Results:

Thus, the molecules AIM2 and AIM3 have a cytostatic action in the different cell lines used (MCF-10A, MDA-MB231 and Hs578).

As indicated in FIG. 9, a treatment with a 2 mM dose inhibits the proliferation of healthy mammary epithelial cells (MCF10A), but also mammary cancer cells (MDA-MB231 and HS578T) (see square point curves with respect to the round untreated controls). However, with the aim of determining the reversibility of these treatments, a 72 h treatment has also been carried out with 2 mM of molecule, followed by a change of medium without adding molecule. In this experiment, it appears that the change of medium makes it possible for the cells to proliferate again and this, in a lot more marked manner concerning healthy mammary epithelial cells (MCF10A). This result makes it possible to consolidate the previous observations demonstrating the non-cytotoxicity of these molecules and therefore the cytostatic effect thereof.

Example 11: Effect Sensitising the Compounds According to the Invention Regarding Chemotherapy in Mammary Tumour Cells (FIG. 10 and FIG. 11)

Breast cancer groups together, in reality, different subcategories based on the expression of 3 molecular markers: the oestrogen receptor (ERa), the progesterone receptor (PR) and the transmembrane receptor belonging to the family of EGF receptors (HER2). Certain tumours are thus named triple negative, as they express none of the 3 molecular markers. This type of tumour poses numerous problems in the treatment thereof due to:

the insensitivity thereof to chemotherapy agents commonly used in the treatment of breast cancer the absence of targeted treatment for these tumours.

One of the major challenges in treating breast cancer consists of attempting to re-sensitise triple negative mammary tumours to chemotherapy agents. One of the targeted aims thus consists of restoring the sensitivity of triple negative mammary cancer cells, MDA-MB231, to a chemotherapy agent, tamoxifen.

From a mechanistic standpoint, tamoxifen is a selective modulator of oestrogen receptors (ERa), i.e. that it is fixed specifically on oestrogen receptors, but without activating any signalling pathway. The resistance of MDA-MB231 cells against tamoxifen has been shown as being due to an absence of expression of ERα. In 2000, Yoshida and their colleagues have shown that the hypermethylation of 2 promoter regions (promoter A and B) upstream from the coding gene ERα is inversely correlated to the expression of ERα in the MDA-MB231 cells.

In addition, a treatment using a demethylating agent (5-azadesoxycytidine) has made it possible to reinduce the expression of ERα in the MDA-MB231 cells (link: the synergic inhibitory effect of 5-aza-2-deoxycytidine and tamoxifen on oestrogen receptor alpha negative breast cancer cell lines in vitro).

The results of the use on 5aza cells being very promising, clinical trials have been carried out for the treatment of certain leukaemia associated with a hypermethylation of specific genes. Although the overall survival of patients has clearly improved, the fact remains that the use of 5-azadesoxycytidine is associated with heavy side effects (neutropenia, thrombocytopenia, anaemia, pyrexia), due to the absence of specificity of action of this molecule. Some of the works carried out in cancerology is thus to generate and to study new demethylating agents having an improve action specificity.

It is in this context that the compounds according to the invention have been developed, including the compound AIM2 which has, as the tests above show, a demethylating action, both in vitro and in cellulo.

Faced with this action mode, the Applicant has studied if the compounds according to the invention made it possible to demethylate the promoter of ERα in MDA-MB231 cells, in order to reinduce the expression thereof, and to re-sensitise the cells to tamoxifen.

Initially, the action synergy between the Applicant's molecule AIM2 and tamoxifen has been studied.

Chou-Talalay tests have been carried out by determining the number of cells attached after treatments using the compound AIM2 and/or using tamoxifen.

Protocol: Chou-Talalay AIM2/Tamoxifen Synergism Experiment

For this, MDA-MB231 cells have been seeded in 96-well plate at a cell density of 8000 cells/well in a volume of 100 μL/well. The plate experiment plan is presented in FIG. 10.

The AIM2 treatment is done for 24 h, followed by 48 h of treatment to tamoxifen. At the end of treatments, a crystal violet marking is done in order to count the living cells.

The protocol is as follows:

suction the wells wash the wells with 100 μL of PBS add 50 μL of crystal violet 0.1% and leave to incubate for 30 minutes at ambient temperature rinse 3 times with distilled water add 100 μL of acetic acid 10% per well and leave to incubate while stirring for 10 minutes measure the absorbance at 595 nm in a VICTOR Multilabel Plate Reader (PerkinElmer).

The plate triplicates are averaged out, and the results are expressed according to the untreated control which is fixed at 1 for each condition.

Results:

The results show that the MDA-MB231 cells, which are ER negative, are insensitive to tamoxifen. A treatment with AIM2 induces a decrease in cell viability of the order of 50% from the lowest dose (2000 nM). A pre-treatment by AIM2 followed by a treatment with tamoxifen also induces a decrease of cell viability, which seems more significant than in the presence of the molecule AIM2 only. In order to know if this decrease in cell viability under the AIM2+Tam condition is explained by a synergy between the 2 molecules, the Applicant has used the CompuSync software which is based on the Chou-Talalay method via the median effect principle of the law of mass action.

The equation on which the software is based is as follows:

$fa/fu=⟦(D/Dm)⟧m$ where:

fa and fu correspond respectively to the fractions of the cells affected and unaffected by the treatments;

D and Dm correspond respectively to the dose used and the median dose (1050)

m corresponds to the form of the dose-response curve.

It is sufficient to enter 3 sets of data into the software:

the values corresponding to the effect of the molecule A on the dose given the values corresponding to the effect of the molecule B on the dose given the values corresponding to the effect of the molecule A and of the molecule B on the combination of the doses given.

The software thus generates combination indexes (CI):

if the CI with a combination of dose given is less than 1, thus there is action synergy between the molecule A and the molecule B if the CI with a combination of dose given is greater than 1, thus there is antagonism between the molecule A and the molecule B.

The results (expressed in the form of combination index, or CI) are presented in table 7 below:

TABLE 7

| Dose of AIM2 | Dose of TAM | Combination of dose | Combination index (CI) |
|---|---|---|---|
| 2000 nM | 100 nM | 2100 nM | 0.48 |
| 5000 nM | 250 nM | 5250 nM | 0.42 |

TABLE 7-continued

| Dose of AIM2 | Dose of TAM | Combination of dose | Combination index (Cl) |
|---|---|---|---|
| 10000 nM | 500 nM | 10500 nM | 1.7 |
| 15000 nM | 750 nM | 15750 nM | 0.63 |
| 20000 nM | 1000 nM | 21000 nM | 0.41 |

As the results show, all the combinations of doses (except for the combination 10000 nM of AIM2 and 750 nM of TAM) make it possible to observe a synergy (CI<1) between tamoxifen and AIM2.

These results therefore make it possible to conclude that a pre-treatment using AIM2 makes it possible to sensitise the MDA-MB231 cells to tamoxifen, which are of insensitive base.

Example 12: MTT Test (Viability) to Demonstrate the Effect of the Compounds According to the Invention on the Sensitivity to Anticancer Agents (FIG. 12)

Subsequently, based on the re-sensitisation of MDA-MB231 cells to tamoxifen in the presence of AIM2, the Applicant has studied if a treatment with the compounds AIM2 and AIM3 made it possible to increase the sensitivity of different mammary tumour lines faced with different chemotherapy agents conventionally used: 5-fluorouracile and doxorubicin.

Protocol:

For this, mammary cancer cells, MCF-7, MDA-MB231 and Hs578T, as well as a normal mammary cell line, MCF10A, have been seeded at a density of $1\times10^4$ cells/well in a 96-well plate. After 24 h of seeding, the cells are put into contact with 2 μM of AIM2/3 for 1 hour followed by 50 μM of 5-fluorouracile or 50 ng/mL of doxorubicin for 24 h or 48 hours. Following these treatments, the mediums are removed and 0.5 mg/mL of MTT is added in each well. After 3 hours of incubation at 37° C., 100 μL of SDS 25% is added in each well and the plates are incubated at 37° C. for the whole night. The absorbance is measured at 570 nm. The results presented correspond to the mean±the standard error mean coming from three independent experiments. The differences between the cells treated at different times are significant for a $p<0.05$.

Results:

The results show that a 24 h treatment with AIM2/3 has no significant effect on the viability, regardless of the breast cancer line considered. However, when the treatment with AIM2/3 is followed by a treatment with 5Fu or with doxorubicin, the cell viability decreases significantly, and this in all lines. This effect appears from 24 hours of treatment, but is accentuated even more during treatments of 48 hours.

These results therefore suggest that the compounds according to the invention sensitise the mammary tumour cells to the chemotherapy agents, indicating a possible therapeutic use of these molecules.

Example 13: Proliferation Test Following a Pre-Treatment with AIM2 or AIM3 2 μM 72 h (FIG. 13 and FIG. 14)

Culture Condition:

The different cell lines are cultivated in an incubator at 37° C., 5% $CO_2$ and 95% of humidity according to the following nutritional mediums:

TABLE 8

| Cell line | MDA-MB 231 | MCF10A | T47D R+ doxo |
|---|---|---|---|
| Culture medium | RPMI 1640 (Gibco 32404014) + 2 mM L-Glutamine (Sigma G7513) + 10% FBS (Sigma F7524) | DMEM F12 (Gibco 21041025) + 5% horse serum (Gibco ™ 16050122) + 20 ng/mL EGF (Sigma SRP3027) + 10 μg/mL insulin (Sigma I1881) + 0.5 μg/mL hydrocortisone (Sigma H0888) + 0.1 μg/mL choleric toxin (Sigma C8052) | RPMI 1640 (Gibco 32404014) + 2 mM L-Glutamine (Sigma G7513) + 10% FBS (Sigma F7524) + 10 nM oestradiol (Sigma E2257) + 12.5 ng/mL doxorubicin (Sigma D1515) |

The different culture mediums are supplemented alternatively by 0.1 mg/mL of Gentamicin (Sigma G1272) and 1% of Penicillin-Streptomycin (Sigma P4333).

Foetal bovine serum (FBS) and horse serum are decomplemented beforehand for 30 minutes at 56° C.

The T47D line resistant to doxorubicin is cultivated in the presence of 12.5 ng of doxorubicin/mL in order to maintain the resistance. However, doxorubicin is not added to the culture medium during the pre-treatment phases and the proliferation test.

Pre-Treatment of Cell Lines

The cells are seeded in 100 mm dishes (10 mL medium/dish) for untreated conditions and in 150 mm dishes (20 mL medium/dish) for treated conditions according to the following quantities:

TABLE 9

| | MDA-MB 231 | MCF10A | T47D R+ doxo |
|---|---|---|---|
| Untreated (cells/100 mm dish) | $1.45 \cdot 10^6$ | $5 \cdot 10^5$ | $1.2 \cdot 10^6$ |
| AIM 2 μM 72 h (cells/150 mm dish) | $4.6 \cdot 10^6$ | $2.3 \cdot 10^6$ | $4.2 \cdot 10^6$ |

The cells are then treated for 24 h after seeding with the molecules AIM2 or AIM3 at a concentration of 2 μM for 72 h.

Cell Seeding Following by Pre-Treatment with AIM

The cells are unstuck with 1 mL (10 mm dishes) or 2 mL (150 mm dishes) of trypsin—EDTA 1× for 5 minutes at 37° C. (15 minutes of incubation are necessary to unstick the MCF1OA cells).

The trypsin action is then inhibited by 10 mL of culture medium then the cell suspension is centrifuged at 200G for 5 minutes.

Each button is returned in 10 mL of medium then the cells are counted using a Mallasez cell.

The cells are then seeded in 60 mm dishes (4 mL medium/dish) as follows, and according to experiment plan of FIG. 13:

TABLE 10

| Cell line | MDA-MB 231 | MCF10A | T47D R+ doxo |
|---|---|---|---|
| Cells/dish | $4 \cdot 10^5$ | $2 \cdot 10^5$ | $4 \cdot 10^5$ |

Cell Count

Each day for 72 h, 3 dishes coming from a cell type and a given treatment are counted.

After a washing with 2 mL of PBS, the cells are unstuck with 1 mL of trypsin-EDTA 1× at 37° C. for 10 minutes (20 minutes for the MCF10A line).

Trypsin is then inhibited by adding 4 mL of medium. Then, the cells are buttoned at 200G for 5 minutes.

The buttons are returned in a precise volume of PBS depending on the size of the button.

The cells are correctly separated by several back and forth movements to the P200 and counted using a Mallasez cell.

As FIG. 14 shows, the results obtained indicate that the proliferation inhibition observed following the treatment with AIM2 and AIM3 is reversible in MCF10A cells and not in MDA-MB-231 cells. A reversibility is also observed in T47D R+doxo cells treated with AIM2, but not with AIM3.

Example 14: Study of the Effect of the Treatment of the Molecules AIM1, AIM2, AIM3 and Ru (FIG. 16) at 2 μM on Different Cell Lines for 48 h or 72 h Culture Condition The different cell lines are cultivated in an incubator at 37° C., 5% $CO_2$ and 95% of humidity according to the following nutritional mediums:

TABLE 11

| Cell line | Culture medium |
|---|---|
| MDA-MB 231 | RPMI 1640 (Gibco 32404014) + 2 mM L-Glutamine (Sigma G7513) + 10% FBS (Sigma F7524) |
| T47D | RPMI 1640 (Gibco 32404014) + 2 mM L-Glutamine (Sigma G7513) + 10% FBS (Sigma F7524) + 10 nM oestradiol (Sigma E2257) |
| T47D R+ doxo | RPMI 1640 (Gibco 32404014) + 2 mM L-Glutamine (Sigma G7513) + 10% FBS (Sigma F7524) + 10 nM oestradiol (Sigma E2257) + 12.5 ng/mL doxorubicin (Sigma D1515) |
| U251 | DMEM (Sigma D5796) + 10% FBS (Sigma F7524) + 50 μM NEAA (Gibco 11140050) + 1 mM sodium pyruvate (Gibco 11360070) |
| U87 | DMEM (Sigma D5796) + 10% FBS (Sigma F7524) + 50 μM NEAA (Gibco 11140050) + 1 mM sodium pyruvate (Gibco 11360070) |

The different culture mediums are supplemented alternatively by 0.1 mg/mL of Gentamicin (Sigma G1272) and 1% of Penicillin-Streptomycin (Sigma P4333).

Foetal bovine serum (FBS) and horse serum are decomplemented beforehand for 30 minutes at 56° C.

The T47D line resistant to doxorubicin is cultivated in the presence of 12.5 ng of doxorubicin/mL in order to maintain the resistance, however doxorubicin is not added to the culture medium during the proliferation test.

Experiment Plan

Each cell line is seeded in 96-well plates (100 μL medium/well) according to the following conditions:

TABLE 12

| | Cell line | | | | |
|---|---|---|---|---|---|
| | MDA-MB231 | T47D | T47D R+ doxo | U251 | U87 |
| Cells/well | $10 \cdot 10^3$ | $10 \cdot 10^3$ | $7 \cdot 10^3$ | $5 \cdot 10^3$ | $5 \cdot 10^3$ |

Each treatment condition is carried out in triplicate as indicated in FIG. 15.

The cells are treated with the molecules represented in FIG. 16 (AIM1, AIM2, AIM3 according to the invention and Ru as comparative example) at 2 μM 24 h after seeding.

After 48 h or 72 h of treatment, the medium of each well is removed then a washing is carried out with 100 μL of PBS.

The cells are then fixed with 100 μL of paraformaldehyde 4% for 20 minutes, followed by two washings with 500 μL of PBS.

Crystal Violet Test

The percentage of cells adhered is highlighted by a crystal violet coloration.

100 μL of crystal violet at 0.1% (1/5 dilution in $H_2O$ of the stock solution: 0.5% crystal violet 2% filtered ethanol 0.22 μM) is added in each well.

After 30 minutes of incubation at ambient temperature, the wells are rinsed 3 times with distilled water, then correctly dried by patting on a sheet of absorbent paper.

100 μL of 10% acetic acid is then added to each well.

The plate is stirred until total solubilisation of the crystal violet crystals (around 10 minutes).

The reading of the absorbance is carried out using a 595 nm plate reader (see FIGS. 17 to 20).

Results:

All of these results represented in FIGS. 17 to 20, indicates that the molecules AIM2 and AIM3 induce a significant inhibition of the proliferation of different cell types tested. The molecule AIM1 is also capable of leading to a drop in cell proliferation, even if this is less marked than for the molecules AIM2 and AIM3. However, the molecule (comparative example) called Ru (which corresponds to the molecule AIM2 of which iron is replaced by ruthenium) does not lead to any inhibition of the proliferation under the conditions tested.

The invention claimed is:

1. A pharmaceutical composition comprising an organometallic compound comprising an iron atom bound to two terpyridine groups, having formula (I):

(I)

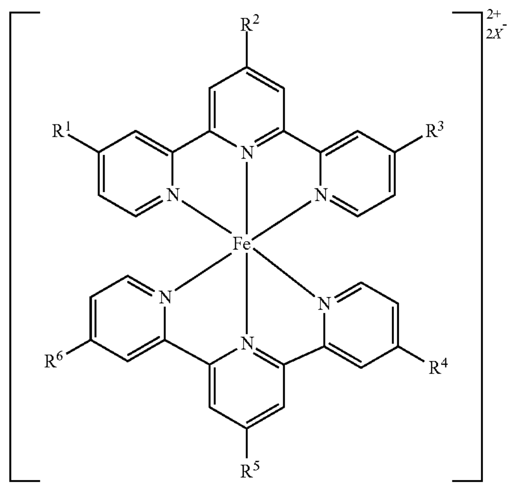

wherein:

each of $R^1$, $R^2$, $R^3$, $R^4$, $R^5$ and $R^6$ is hydrogen;

$X^-$ is a counterion; and a pharmaceutically acceptable carrier.

2. A pharmaceutical composition comprising an organometallic compound comprising an iron atom bound to two terpyridine groups, having formula (I):

(I)

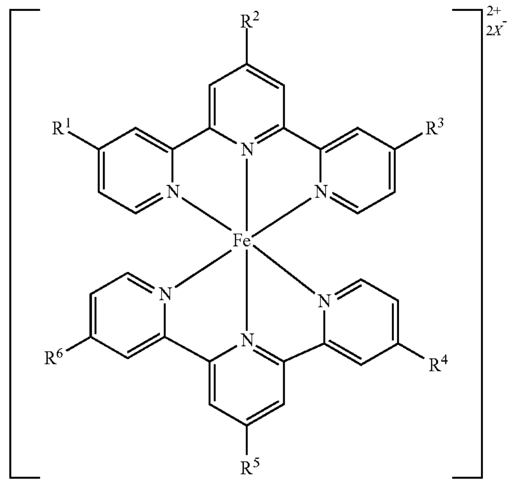

wherein $R^1$, $R^3$, $R^4$, and $R^6$ are identical and are each hydrogen, and $R^2$ and $R^5$ are identical and designate a pyridine radical of following formula (VIII):

(VIII)

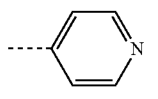

where the dotted line represents a C—C bond between the carbon carried by the pyridine radical and the carbon carried by the terpyridine group of the organometallic compound of formula (I);

$X^-$ is a counterion; and a pharmaceutically acceptable carrier.

3. A method for treatment of cancers selected from glioblastomas, breast cancer, head and neck cancer or pancreatic cancer, comprising administering an effective amount of a pharmaceutical composition to a subject in need thereof, said pharmaceutical composition comprising an organometallic compound comprising an iron atom bound to two terpyridine groups, having formula (I):

(I)

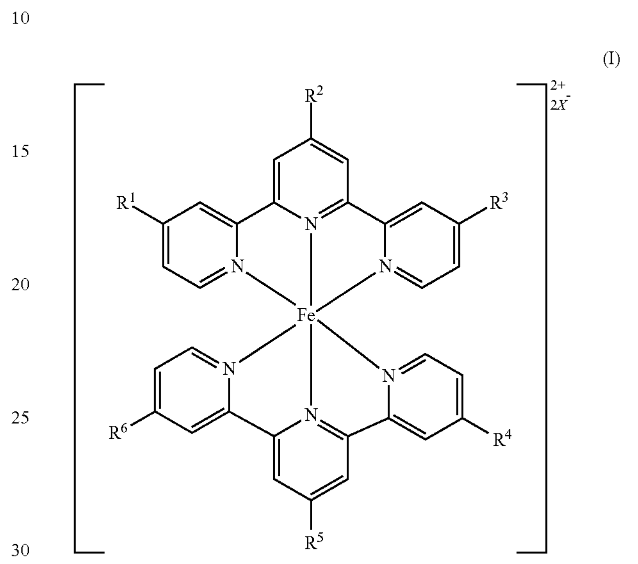

wherein:

$R^1$, $R^2$, $R^3$, $R^4$, $R^5$ and $R^6$, are identical or different and are each independently selected from the group consisting of: a hydrogen atom; and an aromatic cycle selected from the formula (II) below:

(II)

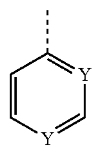

where each Y in formula (II) is independently a CH group or a nitrogen atom;

the dotted line represents a C—C bond at the level of the connection point of the aromatic cycle of formula (II) to the terpyridine groups of the organometallic compound of formula (I);

$X^-$ is a counterion; and a pharmaceutically acceptable carrier.

4. The method for treatment of claim 3, wherein each of $R^1$, $R^2$, $R^3$, $R^4$, $R^5$ and $R^6$ in the formula (I) of the pharmaceutical composition is hydrogen.

5. The method for treatment of claim 3, wherein $R^1$, $R^3$, $R^4$, and $R^6$ of the pharmaceutical composition are identical and are each hydrogen, and $R^2$ and $R^5$ are identical and designate a benzene of following formula (VII):

(VII)

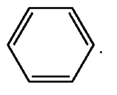

6. The method for treatment of claim 3, wherein $R^1$, $R^3$, $R^4$, and $R^6$ of the pharmaceutical composition are identical and are each hydrogen, and $R^2$ and $R^5$ are identical and designate a pyridine radical of following formula (VIII):

(VIII)

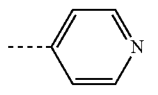

where the dotted line represents a C—C bond between the carbon carried by the pyridine radical and the carbon carried by the terpyridine group of the organometallic compound of formula (I).

7. The method according to claim 3, wherein the pharmaceutical composition is used in combination with at least one f cisplatin, carboplatin, taxol, 5-fluorouracile, tamoxifen and doxorubicin, conditioned and administered in a combined, separate or sequential manner.

8. The method for treatment of claim 3, wherein the cancers are selected from at least one of the following cancer cells:

triple nagative mammary cancer cells MDA-MB 231, mammary cancer cells Hs578T, glioblastoma U87 cells, glioblastoma U251 cells, glioblastoma T98G cells.

9. The method for treatment of claim 7, wherein the pharmaceutical composition is used in pre-treatment, before the administration of 5-fluorouracile or doxorubicin.

10. The method for treatment of claim 9, wherein the cancers are selected from at least one of the following cancer cells: triple nagative mammary cancer cells MDA-MB 231, mammary cancer cells Hs578T.

11. The method for treatment of claim 3, wherein the counterion $X^-$ is selected from the group consisting of: $Cl^-$, $Br^-$ and $I^-$.

* * * * *